United States Patent
To

(10) Patent No.: US 9,610,095 B2
(45) Date of Patent: Apr. 4, 2017

(54) RETRACTOR CANNULA SYSTEM FOR ACCESSING AND VISUALIZING SPINE AND RELATED METHODS

(75) Inventor: John T. To, Newark, CA (US)

(73) Assignee: SPINE VIEW, INC., Fremont, CA (US)

(*) Notice: Subject to any disclaimer, the term of this patent is extended or adjusted under 35 U.S.C. 154(b) by 671 days.

(21) Appl. No.: 12/582,638

(22) Filed: Oct. 20, 2009

(65) Prior Publication Data

US 2010/0121153 A1 May 13, 2010

Related U.S. Application Data

(60) Provisional application No. 61/106,914, filed on Oct. 20, 2008.

(51) Int. Cl.
*A61B 17/34* (2006.01)
*A61B 10/06* (2006.01)
(Continued)

(52) U.S. Cl.
CPC .......... *A61B 17/3417* (2013.01); *A61B 10/06* (2013.01); *A61B 1/3135* (2013.01); *A61B 5/0084* (2013.01); *A61B 8/12* (2013.01); *A61B 17/0218* (2013.01); *A61B 90/361* (2016.02); *A61B 2017/003* (2013.01); *A61B 2017/00261* (2013.01); *A61B 2017/320064* (2013.01); *A61B 2017/3419* (2013.01)

(58) Field of Classification Search
USPC ............. 606/45–46, 206; 600/104, 201–219; 604/164.01, 164.03, 164.1, 164.06
See application file for complete search history.

(56) References Cited

U.S. PATENT DOCUMENTS

| 4,319,563 A | 3/1982 | Kubota |
| 4,557,255 A | 12/1985 | Goodman |

(Continued)

FOREIGN PATENT DOCUMENTS

| DE | 100 37 421 A1 | 5/2002 |
| EP | 0 316 816 A1 | 5/1989 |

(Continued)

OTHER PUBLICATIONS

International Search Report mailed on Dec. 11, 2009, for PCT Patent Application No. PCT/US09/16575, filed on Oct. 20, 2009, 4 pages.

(Continued)

*Primary Examiner* — Nicholas Woodall
(74) *Attorney, Agent, or Firm* — Morrison & Foerster LLP; Ross M. Carothers

(57) ABSTRACT

Retractor cannula systems may be used for accessing and visualizing the spine and related methods of treatment, including a forward-looking retractor cannula system for creating a working space and the retractor cannula system having atraumatic dissection capability to allow visualization in spine. The devices and methods described may be used, for example, to perform annulus repair, herniated disc excision, and denervation of neurological tissue; to dispense pharmacological agents and/or cell or tissue therapy agents; to diagnose disc degeneration and bony degeneration, spinal stenosis, and nucleus decompression, and to perform disc augmentation.

27 Claims, 23 Drawing Sheets

(51) Int. Cl.
*A61B 1/313* (2006.01)
*A61B 5/00* (2006.01)
*A61B 8/12* (2006.01)
*A61B 17/02* (2006.01)
*A61B 17/00* (2006.01)
*A61B 17/32* (2006.01)
*A61B 90/00* (2016.01)

(56) References Cited

U.S. PATENT DOCUMENTS

| | | | |
|---|---|---|---|
| 4,607,619 A * | 8/1986 | Seike et al. | 600/106 |
| 4,836,205 A * | 6/1989 | Barrett | A61B 17/0469 606/144 |
| 4,887,612 A | 12/1989 | Esser et al. | |
| 4,890,615 A * | 1/1990 | Caspari | A61B 17/0469 606/139 |
| 5,007,908 A | 4/1991 | Rydell | |
| 5,066,288 A | 11/1991 | Deniega et al. | |
| 5,172,700 A | 12/1992 | Bencini et al. | |
| 5,228,451 A | 7/1993 | Bales et al. | |
| 5,235,966 A * | 8/1993 | Jamner | 600/204 |
| 5,258,026 A | 11/1993 | Johnson et al. | |
| 5,313,962 A | 5/1994 | Obenchain | |
| 5,327,908 A | 7/1994 | Gerry | |
| 5,342,389 A | 8/1994 | Haber et al. | |
| 5,354,302 A | 10/1994 | Ko | |
| 5,373,854 A | 12/1994 | Kolozsi | |
| 5,454,365 A | 10/1995 | Bonutti | |
| 5,476,479 A | 12/1995 | Green et al. | |
| 5,500,019 A | 3/1996 | Johnson et al. | |
| 5,509,922 A | 4/1996 | Aranyi et al. | |
| 5,535,754 A | 7/1996 | Doherty | |
| 5,558,620 A | 9/1996 | Heckele et al. | |
| 5,562,694 A | 10/1996 | Sauer et al. | |
| 5,599,279 A | 2/1997 | Slotman et al. | |
| 5,626,609 A | 5/1997 | Zvenyatsky et al. | |
| 5,665,100 A | 9/1997 | Yoon | |
| 5,690,606 A | 11/1997 | Slotman | |
| 5,700,276 A * | 12/1997 | Benecke | A61B 17/1608 606/206 |
| 5,762,613 A | 6/1998 | Sutton et al. | |
| 5,776,075 A | 7/1998 | Palmer | |
| 5,785,647 A | 7/1998 | Tompkins et al. | |
| 5,797,906 A | 8/1998 | Rhum et al. | |
| 5,797,958 A | 8/1998 | Yoon | |
| 5,843,000 A | 12/1998 | Nishioka et al. | |
| 5,922,002 A | 7/1999 | Yoon | |
| 5,984,919 A | 11/1999 | Hilal et al. | |
| 5,984,939 A | 11/1999 | Yoon | |
| 6,053,933 A * | 4/2000 | Balazs et al. | 606/205 |
| 6,066,102 A | 5/2000 | Townsend et al. | |
| 6,083,150 A | 7/2000 | Aznoian et al. | |
| 6,129,683 A | 10/2000 | Sutton et al. | |
| 6,152,871 A | 11/2000 | Foley et al. | |
| 6,228,022 B1 | 5/2001 | Friesem et al. | |
| 6,394,964 B1 | 5/2002 | Sievert, Jr. et al. | |
| 6,497,651 B1 * | 12/2002 | Kan et al. | 600/114 |
| 6,679,833 B2 | 1/2004 | Smith et al. | |
| 6,776,780 B2 | 8/2004 | Mulier et al. | |
| 6,808,491 B2 | 10/2004 | Kortenbach et al. | |
| 6,818,007 B1 * | 11/2004 | Dampney | A61B 17/29 606/205 |
| 6,849,078 B2 | 2/2005 | Durgin et al. | |
| 6,851,430 B2 | 2/2005 | Tsou | |
| 6,945,933 B2 | 9/2005 | Branch et al. | |
| 6,966,919 B2 | 11/2005 | Sixto, Jr. et al. | |
| 7,001,405 B2 | 2/2006 | Kieturakis et al. | |
| 7,105,000 B2 | 9/2006 | McBrayer | |
| 7,204,851 B2 | 4/2007 | Trieu et al. | |
| 7,207,949 B2 | 4/2007 | Miles et al. | |
| 7,214,236 B2 | 5/2007 | Kieturakis et al. | |
| 7,261,688 B2 | 8/2007 | Smith et al. | |
| 7,347,863 B2 | 3/2008 | Rothe et al. | |
| 7,455,639 B2 | 11/2008 | Ritland | |
| 7,473,253 B2 | 1/2009 | Dycus et al. | |
| 7,582,058 B1 | 9/2009 | Miles et al. | |
| 2001/0056280 A1 | 12/2001 | Underwood et al. | |
| 2002/0062136 A1 | 5/2002 | Hillstead et al. | |
| 2002/0099373 A1 * | 7/2002 | Schulze et al. | 606/51 |
| 2003/0009227 A1 | 1/2003 | Lambrecht et al. | |
| 2003/0065351 A1 | 4/2003 | Hess et al. | |
| 2004/0122461 A1 * | 6/2004 | McGuire et al. | 606/184 |
| 2005/0222681 A1 | 10/2005 | Richley et al. | |
| 2005/0251192 A1 | 11/2005 | Shluzas et al. | |
| 2006/0167987 A1 * | 7/2006 | Yamane | 709/203 |

FOREIGN PATENT DOCUMENTS

| | | |
|---|---|---|
| EP | 0 316 816 B1 | 5/1989 |
| EP | 1 036 544 A1 | 9/2000 |
| WO | WO-83/03189 A1 | 9/1983 |
| WO | WO-97/41777 A1 | 11/1997 |
| WO | WO-2004/037097 A1 | 5/2004 |

OTHER PUBLICATIONS

Written Opinion mailed on Dec. 11, 2009, for PCT Patent Application No. PCT/US09/16575, filed on Oct. 20, 2009, 7 pages.

* cited by examiner

RETRACTOR CANNULA SYSTEM FOR ACCESSING AND VISUALIZING SPINE AND RELATED METHODS

CROSS-REFERENCE TO RELATED APPLICATIONS

This application claims priority under 35 U.S.C. §119(e) to U.S. Provisional Application No. 61/106,914, filed Oct. 20, 2008, the disclosure of which is hereby incorporated by reference in its entirety. This application is also related to U.S. application Ser. No. 12/199,706, filed Aug. 27, 2008, which is also hereby incorporated by reference in its entirety.

BACKGROUND

Injured intervertebral discs are generally treated with bed rest, physical therapy, modified activities, and pain medications for substantial treatment durations. There are also a number of treatments that attempt to repair injured intervertebral discs and to avoid surgical removal of injured discs. For example, disc decompression is a procedure used to remove or shrink the nucleus, thereby decompressing and decreasing the pressure on the annulus and nerves. Less invasive procedures, such as microlumbar discectomy and automated percutaneous lumbar discectomy, remove the nucleus pulposus of a vertebral disc by aspiration through a needle laterally inserted into the annulus. Another procedure involves implanting a disc augmentation device in order to treat, delay, or prevent disc degeneration. Augmentation refers to both (1) annulus augmentation, which includes repair of a herniated disc, support of a damaged annulus, and closure of an annular tear, and (2) nucleus augmentation, which includes adding or removing material to the nucleus. Many conventional treatment devices and techniques, including open surgical approaches, involve muscle dissection or percutaneous procedures to pierce a portion of the disc under fluoroscopic guidance, but without direct visualization. Several treatments also attempt to reduce discogenic pain by injecting medicaments or by lysing adhesions in the suspected injury area. However, these devices also provide little in the form of tactile sensation for the surgeon or allow the surgeon to atraumatically manipulate surrounding tissue. In general, these conventional systems rely on external visualization for the approach to the disc and thus lack any sort of real time, on-board visualization capabilities.

Accurately diagnosing back pain is often more challenging than expected and often involves a combination of a thorough patient history and physical examination, as well as a number of diagnostic tests. A major problem is the complexity of the various components of the spine, as well as the broad range of physical symptoms experienced by individual patients. In addition, the epidural space contains various elements such as fat, connective tissue, lymphatics, arteries, veins, blood, and spinal nerve roots. These anatomical elements make it difficult to treat or diagnose conditions within the epidural area because they tend to collapse around any instrument or device inserted therein. This may reduce visibility in the epidural space, and may cause inadvertent damage to nerve roots during device insertion. Also, the insertion of a visualization device may result in blocked or reduced viewing capabilities. As such, many anatomical elements within the epidural space may limit the insertion, movement, and viewing capabilities of any access, visualization, diagnostic, or therapeutic device inserted into the epidural space.

BRIEF SUMMARY

Some embodiments herein relate to cannula retractor systems for accessing and visualizing the spine and related methods of treatment. In some examples, the retractor assembly may be used to create a working space and/or having an atraumatic configuration that may be used to displace or dissect tissue. In some further examples, the retractor assembly may comprise a set of movable elements or jaws about the distal end of a cannula which may be opened to create a larger visualization field and working space. Endoscopes and various therapeutic tools located in the cannula may be used as the jaws are kept open, or in some instances, when the jaws are in a closed position. The devices and methods described herein may be used, for example, to perform annulus repair, herniated disc excision, denervation of neurological tissue, or the removal of bony material from the spine. The devices and methods may also be used to deliver pharmacological agents and/or cell or tissue therapy agents, to diagnose disc degeneration and bony degeneration, to treat spinal stenosis, and to perform nucleus decompression, or disc augmentation.

In one embodiment, a retractor cannula device may comprise a tubular body with a retractor assembly located at the distal end of the tubular body. The tubular body may have at least one lumen configured to hold an endoscopic or other visualizing system, and the retractor assembly may comprise a first closed configuration and a second open configuration. In some embodiments, the at least one lumen may be configured to removably receive the endoscopic system. The retractor cannula device may also comprise an endoscopic system. In one embodiment, the retractor assembly comprises at least one movable element, where the at least one movable element has a curved surface. The curved surface of the at least one movable element may comprise a first point having a first tangent and a second point having a second tangent that is perpendicular to the first tangent. In some embodiments, the curved surface of each of the movable elements may be uniformly oriented around a longitudinal axis of the retractor cannula device to generally form a rounded tip in the first closed configuration. In other embodiments, the curved surface of each of the movable elements may be non-uniformly oriented around a longitudinal axis of the retractor cannula device to form a tapered tip in the first closed configuration. In some embodiments, the tapered tip comprises a linear taper region. In certain embodiments, the curved surface of at least one movable element is non-uniformly and asymmetrically oriented around a longitudinal axis of the retractor cannula device to form an angled tip. In some embodiments, the angled tip may be oriented across a longitudinal midline of the retractor assembly. In some embodiments, the at least one movable element may comprise an optically transparent material. Some embodiments of a retractor assembly may comprise at least two movable elements.

In some embodiments of a retractor cannula device, the cross-section of the retractor assembly perpendicular to a longitudinal axis of the device may comprise a non-circular configuration. In some embodiments, the cross-section of the retractor assembly perpendicular to a longitudinal axis of the device may comprise at least one linear region. In some embodiments of a retractor assembly comprising at least one movable element, the at least one movable element may comprise a convex outer surface. In some embodiments, the at least one movable element may comprise a concave inner surface.

In some embodiments of a retractor cannula device, the retractor assembly may comprise at least one movable element and at least one fixed element, where the movable and the fixed element(s) may comprise an optically transparent material. In one embodiment, when the retractor assembly is in the first closed configuration, the at least one movable element and the at least one fixed element may form a side aperture. In some embodiments, the at least one fixed element is distal to the tubular body and may be oriented parallel to a longitudinal axis of the device.

Some embodiments of a retractor cannula device may further comprise a handle at the proximal end of the tubular body. The handle may comprise a pivot member and a device-locking member. In some embodiments, the handle may further comprise a pivot member lock configured to restrict the movement of the pivot member. Some embodiments of a handle may also comprise resistance mechanisms to set the actuation force of the pivot member. In some embodiments, the device-locking mechanism may be configured to secure an endoscopic system. Some embodiments of a handle may comprise one or more ports. Some embodiments of a handle may additionally or alternatively comprise one or more lumens. In one embodiment, the at least one port may be configured as a flush port, and/or at least one more port may be a visualization port in communication with the at least one lumen configured to hold an endoscopic system.

In one embodiment, a method of accessing a portion of the spine including percutaneously approaching a portion of the spine with an instrument having direct visualization capability, providing an access to a portion of the spine using the instrument, and positioning a device about the portion of the spine using the instrument. In a further embodiment, the instrument may comprise a retractor assembly and the method may include passing the retractor assembly in a closed configuration to a spine region, and actuating the retractor assembly to an open configuration. In another embodiment, the retractor assembly may comprise a material or marker to augment visualization of the structure by imaging modalities used inside or outside of the body. A diagnostic device, a therapy delivery device, a stimulation device or a pharmacological therapy device may be also inserted into the instrument and to the spine region. In another embodiment, the method includes implanting a device using the direct visualization capability of the instrument. In still other embodiments, a method includes providing access to a portion of the spine, such as the spinal epidural space, the annulus, the layers of annulus, the disc nucleus, the facet joints, the foramen, or the spine musculature. In still another embodiment, the method also includes receiving visualization information from an imaging modality located outside of the body such as fluoroscopy, magnetic resonance imaging, and/or computer tomography. In still other embodiments, the method includes using the direct visualization capability of the instrument to maneuver the instrument between a spinal nerve root, the spinal dura and nerve tissue and other tissues, and/or atraumatically manipulating the spinal nerve root or other soft tissue. In yet another embodiment, the method includes using the instrument to deliver disc augmentation devices, nucleus augmentation devices or disc excision devices. In another embodiment, the instrument may be used for diagnostic purposes.

In one embodiment, a retractor cannula system may comprise at least two interlocking jaws that have a substantially rounded or curved geometry when in the closed configuration. Following positioning of the retractor cannula system about the target site, the jaws of the retractor assembly may be placed in the open configuration and may be used as an atraumatic tool for dissection and/or a displacing tissue to create working space, thereby enhancing visualization of other surrounding structures. In one embodiment, the retractor assembly is a forward-looking structure so that the distal tip of the retractor assembly may push obstructive tissue away from the scope, and the distal tip of the retractor assembly may provide a depth of view between the scope and the targeted sites to be treated.

One embodiment is directed to a retractor cannula device comprising a multi-lumen elongate shaft, a retractor assembly attached at its distal end of the shaft, wherein the retractor assembly comprises at least two jaws that are pivotably coupled to the distal section of the elongate shaft, capable of a first closed configuration and a second open configuration, wherein the second open configuration may displace tissue, expand the visual field, and/or maintain a working field. In one embodiment, the jaws of the retractor assembly form a rounded shape or tapered shape tip when in the closed configuration. In other embodiments, the retractor assembly may have any of a variety of other shapes, tapered or not. In certain embodiments, the jaws may be made of an optically opaque material or an optically transparent material. In some examples, an endoscope or fiber optic line within the elongate shaft with an optically transparent retractor assembly may be used visualize the surrounding tissue when the jaws are in either the open and closed configuration.

Some embodiments may also comprise a retractor assembly catheter having a proximal portion and a distal portion and one or more lumens, wherein said proximal portion contains 3 separate lumens, one of said lumens being suitable for allowing the passage of an endoscope, one of said lumens being suitable for aspiration and/or irrigation, and the other lumen being suitable for allowing passage of therapeutic instruments or infusion of medications. In other embodiments, the inner edge of the jaws may be hinged to allow an angle to be formed in the open configuration, the angle being anywhere from about 1 degree to about 359 degrees. In certain embodiments, the hinge may be a rivet or screw around which the jaws rotate, and in certain embodiments, the hinge may be a living hinge involving the flexion of a pliable material.

In another embodiment, an apparatus and method for treating spinal disorders is provided, which comprises introducing a retractor cannula device having direct visualization capability into a patient, steering the retractor cannula device to a position about the spinal targeted site using visualization information provided by an endoscope or other visualization device in combination with the retractor cannula device, dissecting and/or displacing tissue with the retractor assembly of the retractor cannula device to create a working space, and using the retractor cannula device to provide a disc augmentation device in the working space for treating disc degeneration.

In another embodiment, a method for treating intervertebral disc degeneration in a spine of a body includes making an incision into a skin of the body, introducing a retractor cannula device that permits direct visualization into a portion of the spine, introducing a therapy device into retractor cannula device, and treating the disc degeneration.

In another embodiment, a method for treating intervertebral disc degeneration includes introducing a retractor cannula device that permits direct visualization capability into a portion of the spine, steering the retractor cannula device to a position adjacent to a disc or neural tissue using visualization information provided by a visualization system, displacing the neural tissue or other tissues with the retractor cannula device to create a working area, using the retractor cannula device to deliver a therapy device for treating intervertebral disc degeneration, and treating the disc degeneration. The visualization system may be used in conjunction with the retractor cannula device or may be integrated with the retractor cannula device. In some embodiments, the therapy device is a nucleus decompression device configured to inject substances and/or remove material from the nucleus, the annulus, or one or more fragmented segments of the vertebral disc. In some embodiments, a therapy device may be used to shrink a portion of the nucleus or the annulus. Treating the disc degeneration may also comprise repairing a herniated disc, supporting a damaged annulus, adding or removing material with respect to the nucleus, annulus or a bony structure, and/or sealing an annulus. In one embodiment, displacing the tissues comprises actuating the retractor structure of the retractor cannula device to an open or wider configuration.

In another embodiment, a system for intervertebral disc augmentation includes a retractor cannula device configured to provide access for a disc augmentation device to an intervertebral disc. In one embodiment, the retractor cannula device includes an elongate body, one or more movable jaws, a direct visualization device, and at least one working channel. The jaws may be coupled to the elongate body in any suitable hinge configuration or other articulation, and is configured to at least transition from a closed to and open configuration. In one or more of the embodiments, the jaws may be configured to displace tissues in the spinal area, and to create a working area. A direct visualization device inserted into the retractor cannula device or may be integral with the retractor cannula device, using a fiber optic line or an imaging sensor located on the direct visualization device. In some embodiments, the augmentation device comprises at least one mesh, cage, barrier, patch, scaffold, sealing means, hydrogel, silicone, growth factor, or combination thereof. In some embodiments, the augmentation device may be an ablation device, a balloon, or a temperature-controlled energy element, for example. The energy element may be a thermal energy device that delivers resistive heat, radiofrequency, coherent and incoherent light, microwave, ultrasound or liquid thermal jet energies to the nucleus.

In another embodiment, a method of diagnosing disc degeneration in a patient includes introducing a retractor cannula device permitting direct visualization capability into a portion of the spine, steering the retractor cannula device using visualization information provided by the retractor cannula device, displacing the neural tissues or other tissues with the retractor cannula device to create a working area, and assessing the targeted site. The retractor cannula device may comprise a material or marker to enhance visualization of the structure using an imaging modality outside of the body. The method may include receiving visualization information from an imaging modality outside of the body, such as fluoroscopy, CT and/or magnetic resonance imaging. The visualization information may also be provided by an image generated by a sensor located on the visualization device. The retractor cannula device may also include a sensor for collecting diagnostic data.

In another embodiment, a kit for augmenting the intervertebral disc may include at least one disc augmentation device, a retractor cannula device having a tapered shape retractor assembly at its distal tip, an endoscopic mechanism having direct visualization capabilities, and instructions for locating the at least one disc augmentation device using the retractor cannula device. The kit for decompressing the nucleus of an intervertebral disc may also include at least one nucleus decompression device, a retractor cannula device at its distal tip that permits direct visualization using an endoscope or other visualization system, and instructions for decompressing the nucleus of an intervertebral disc using the retractor cannula device.

In another embodiment, a method for treating intervertebral disc degeneration includes introducing a retractor cannula device permitting direct visualization into a portion of the spine using a visualization mechanism, displacing the spinal tissue with the retractor cannula device to create a working area, and using the retractor cannula device to deliver a stimulation electrode device for treating intervertebral disc degeneration. In one or more of the embodiments, the retractor cannula device may be steered to a position about the spinal column by direct visualization of the visualization mechanism. The method may also include, steering the retractor cannula device using visualization information provided by the visualization mechanism, displacing the tissues in spinal area with a portion of the retractor cannula device to create a working area, and using the retractor cannula device to deliver a stimulation electrode device for treating intervertebral disc degeneration. The visualization mechanism, such as an endoscope, may be placed into the retractor cannula device or may be integrally formed with the retractor cannula device.

In another embodiment, a retractor cannula device for assessing a target site within the body may include a multi-lumen elongate shaft and a retractor assembly attached at a distal end of the shaft, wherein the retractor assembly is comprised of at least two jaws coupled to the shaft via any suitable articulation, including hinge structures, such that the jaws may have a closed configuration and an open configuration. In the closed configuration, the jaws may mate with one another such that a substantially smooth and rounded tip is formed. In the open configuration, the jaws are moved outward, increasing the angle between their inner edges, which may be used to dilate tissue and to increase the field of view.

In another embodiment, a retractor cannula device for visualizing a target site within body may include a proximal portion and a distal portion, at least three lumens positioned within the proximal portion, wherein at least one lumen is configured for insertion of an endoscope, and at least one lumen is suitable for allowing passage of therapeutic instruments or injection of medications. A retractor assembly may be attached to the distal portion of the retractor cannula device, and at least part of the distal portion of the retractor cannula device may be configured such that in at least one configuration, the jaws of the retractor assembly may allow direct visualization. In some embodiments, the jaws of the retractor assembly are constructed of opaque or transparent materials, for example any polyester copolymer (PETG, PETE), nylon, urethane, polycarbonate, acrylic, silicone, and/or glass.

In another embodiment, a retractor cannula device may include an elongate shaft having a proximal portion and a distal portion, wherein the proximal portion contains four separate lumens, one of said lumens being configured for the passage of the endoscope and/or irrigation therethrough, one of said lumens being configured for the passage of therapeutic instruments and/or aspiration, one of the said lumens being configured for the actuating members that manipulate the jaws of the retractor assembly, and one of said lumens for additional aspiration or irrigation. The distal portion of the retractor cannula device may comprise lumen openings, with one of said lumen openings in continuity with the lumen for the endoscope and/or irrigation, one of said lumen openings in continuity with the lumen for therapeutic instruments and/or aspiration, and one of said lumen openings in continuity with the lumen for additional aspiration or irrigation. The use of any one lumen need not be limited to a particular instrument or procedure, and may be used differently from the exemplary embodiments disclosed herein. In some embodiments, two or more lumens may be used for the same purpose during a procedure.

In one embodiment, a minimally invasive spinal endoscopy system is provided, comprising a tubular shaft with a slotted flexion zone, at least two slidable control wires, a proximal end, a distal end, at least two irrigation channels, at least one non-circular instrument channel, and a visualization channel. In some examples, the tubular shaft may have an average diameter of less than about 3.5 mm, or less then 2.5 mm, or even less than 1.5 mm. The system may further comprise an actuator attached to at least two slidable control wires, a housing enclosing the proximal end of the tubular shaft and at least a portion of the actuator, and a retractor assembly. The minimally invasive spinal endoscopy system may also further comprise a guidewire, a dilator, an introducer sheath, a tissue debrider, a retractor assembly, a coagulation probe, and an infusion cannula configured for insertion into at least one instrument channel.

In another embodiment, a minimally invasive device for use in a body is provided, comprising a tubular body comprising a proximal end, a distal end, a first lumen therebetween, and a retractor assembly control lumen, and a retractor assembly with at least two jaws in communication with the retractor assembly control lumen, a proximal end, and a distal end. The retractor assembly may also have a closed configuration with a reduced profile and an open configuration with an enlarged profile. In some examples, the retractor assembly may be biased to the closed configuration, the open configuration, or a third configuration. The retractor assembly may comprise a rounded or tapered shape.

In one embodiment, a kit for performing a medical procedure may be provided, comprising a cannula with a cannula lumen configured to accommodate an endoscope, a distal retractor assembly with a working space, and a rotatable tissue removal device configured for insertion through the cannula and into the working space of the distal retractor assembly. The kit may also further comprise an endoscope configured for insertion into the cannula.

In another embodiment, a method for minimally invasively accessing a body site is provided, comprising providing a tubular body with a retractor assembly located at a distal ned of the tubular body and protruding from the distal end of the tubular body, where retractor assembly has a closed and an open configuration, and the tubular body comprises a viewing lumen to retain an endoscope and a working space distal to the viewing lumen, inserting a tubular body toward a non-vascular target site in a body, urging the retractor assembly of the tubular body into an open configuration while in the body, and visualizing the non-vascular target site from the tubular body and through the lumen of the retractor assembly. The method may also optionally comprise inserting an endoscopic device into the tubular body. The method may also include advancing the distal end of the tubular body toward a neural structure in contact with a non-neural structure, and displacing the neural structure from the non-neural structure using the retractor assembly. The method may also comprise orienting the working space of the retractor assembly with the non-vascular target site. In some embodiments, the method may additionally or alternatively comprise urging the retractor assembly from a closed to an open configuration while in the body, and visualizing the non-vascular target site from the tubular body and through a working space of the retractor assembly.

Another embodiment comprises a method for treating intervertebral disc degeneration in a spine, which may involve introducing a retractor cannula device having direct visualization capability into a portion of a spine, wherein the retractor cannula device contains at least one lumen configured to encase an endoscope, urging the retractor assembly cannula into an open configuration to create a forward looking capability to enhance visualization and displacement of tissues, and introducing a therapy device into the retractor cannula device to treat disc degeneration. The therapy device may be any of a variety of therapy devices, including implants configured to provide structural support to a disc annulus of the spine, device configured to seal a torn annulus, and/or those instruments that add and/or remove additional material to the nucleus.

In some embodiments, a method for treating intervertebral disc degeneration in a spine of a body may comprise making an incision into a skin of the body, introducing a retractor cannula device with a direct visualization component into a portion of the spine, urging or manipulating the retractor assembly into an open configuration to create a forward looking capability to enhance visualization and displacement of tissues, introducing a therapy device into the retractor cannula device, and treating the disc degeneration. In some embodiments, the method may additionally or alternatively comprise manipulating the retractor assembly from a closed to an open configuration to provide an enlarged working space to augment tissue visualization and displacement.

In another embodiment, a method for treating intervertebral disc degeneration may comprise introducing a retractor cannula device having direct visualization capability into a portion of the spine, steering the retractor cannula device to a position adjacent an outer surface of the disc or nervous tissues using visualization information provided by the retractor cannula device, displacing the nervous tissues or other tissues with a portion of the retractor cannula device to create a working area, using the retractor cannula device to deliver a therapy device for treating intervertebral disc degeneration, and treating the disc degeneration. The therapy device may be a nucleus decompression device to remove a portion of the nucleus, annulus, or fragmented segments, or a therapy device shrinks a portion of the nucleus or annulus, for example. More than one therapy device may be provided or used with the retractor cannula device. Treatment of the disc degeneration may comprise repairing a herniated disc, supporting a damaged annulus, sealing an annulus, adding material or removing material with respect to the nucleus or annulus, and/or dilating or displacing spinal tissue using the retractor cannula device.

BRIEF DESCRIPTION OF THE DRAWINGS

The embodiments herein are best understood from the following detailed description when read in conjunction with the accompanying drawings. It is emphasized that, according to common practice, the various features of the drawings may or may not be to-scale. On the contrary, the dimensions of the various features may be arbitrarily expanded or reduced for clarity. In some figures, the same reference numerals may be used to denote related structures in different embodiments or examples. Included in the drawings are the following figures:

FIGS. 4A and 4B are superior views of the tapered retractor assembly; FIG. 4C is a side view of the retractor assembly from FIGS. 4A and 4B. FIG. 4D is a side view of the tapered retractor assembly in both the closed (dotted lines) and open (solid lines) configuration. FIG. 4E is a perspective view of the retractor assembly in FIG. 4A. FIG. 4F is a component view of a tapered retractor element.

DETAILED DESCRIPTION

Conventional systems often rely on external visualization such as fluoroscopy and CT scanning for the approach to the disc, and thus lack any sort of real time, on-board visualization capabilities. Also, existing devices provide little in the form of tactile sensation for the surgeon and do not allow the surgeon to atraumatically manipulate surrounding tissue.

There is a need, therefore, for minimally invasive techniques and systems that provide the capability to diagnose or repair the spine using direct visualization while minimizing damage to surrounding anatomical structures and tissues. There is also a need for a method and device that allows a physician to effectively enter the epidural space of a patient, clear an area within the space to enhance visualization and use the visualization capability to diagnose and treat the disc injury.

The embodiments disclosed herein will be more clearly understood and appreciated with respect to the following Detailed Description, when considered in conjunction with the accompanying Drawings.

I. Retractor Cannula Device

Figure 1:
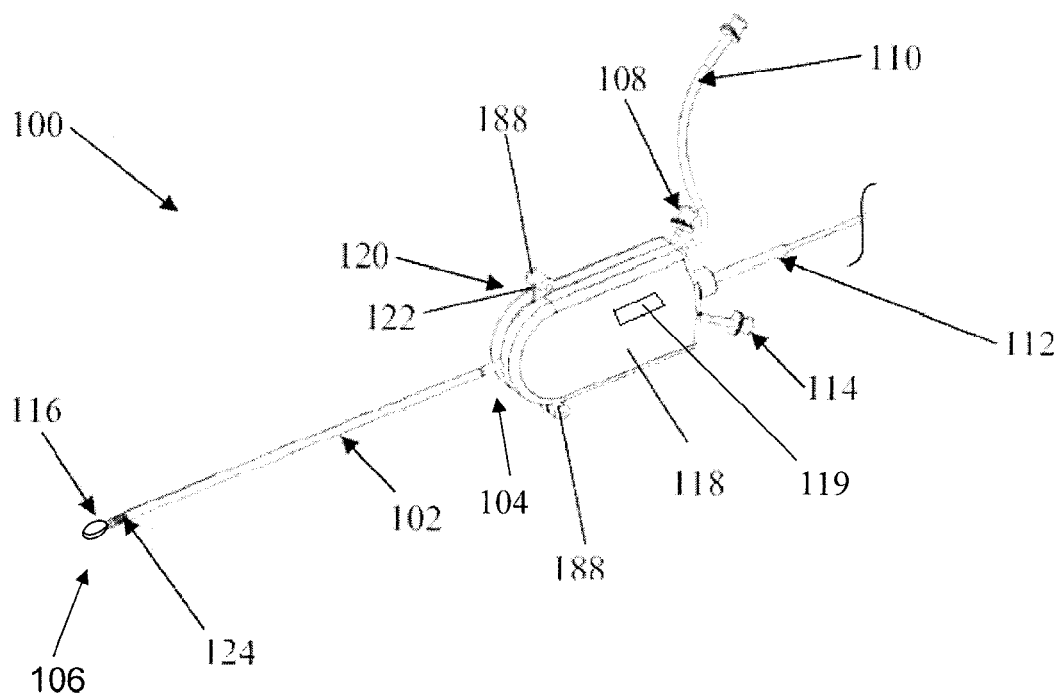
FIG. 1 is a perspective view of one variation of a retractor cannula device.
Figure 2:
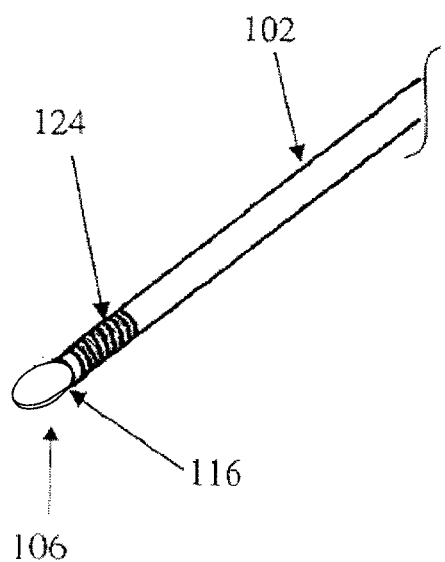
FIG. 2 is a perspective view of a distal portion of the retractor cannula device from FIG. 1.

A retractor cannula device may be used to deliver devices and therapies, such as devices for visualization/imaging, aspiration, irrigation, medication infusion, spinal disc augmentation, nucleus decompression, ablation, implantation, and the like. FIGS. 1 and 2 depict one embodiment of a retractor cannula device 100, which may comprise a tubular body 102 with a proximal end 104 and a distal end 106, a retractor assembly 116, and a handle 118. The proximal end of the tubular body 102 may be associated with one or more ports 108, 110, 112, and 114 via the handle 118. The distal end 106 may be coupled to the retractor assembly 116, one example of which is shown in FIG. 2. Retractor assembly 116 may be coupled to the tubular body 102 via a flexible region 124 that is configured to permit flexion of the distal end 106. The retractor assembly 116, examples of which are described in greater detail below, may be used to create working space for the insertion and movement of devices and direct visualization of a target body region. Space may be created by dissecting, deforming, manipulating, securing or atraumatically displacing surrounding tissue, structure, or anatomical features, for example. The retractor assembly 116 may have two or more configurations, for example, an open configuration and a closed configuration. In some embodiments, a retractor assembly may be configured to be advanced over a guide element, e.g., a guide wire, which may facilitate navigation of the retractor cannula device to the targeted body region. The ports 108, 110, 112, and 114 may be in communication with one or more channels of the retractor assembly 116 via one or more lumens or channels in the tubular body, and may be configured for any of a variety of usages, including but not limited to infusion/drainage/suction of fluids or materials, insertion/removal or supporting an endoscope, fiber-optic or visualization device, opening/closing of the retractor assembly, and for insertion or removal or support of other instruments or tools. Atraumatic displacement of the tissue surrounding the targeted body region by the retractor assembly 116 may increase the angle of view of the surrounding structures from an endoscope or other visualization assembly located in the device 100, and may also help to improve the images taken by an endoscope, e.g., by displacing structures a certain focal distance from the endoscope.

The handle 118 may be any suitable handle structure, and may be provided at the proximal end 104 of the tubular body 102. In addition to supporting the ports 108, 110, 112, and 114, the handle 118 may facilitate manipulation and use of the retractor cannula device through one or more actuators, for example, buttons, slide actuators, dials, levers, and the like. In the particular embodiment depicted in FIG. 1, the handle comprises a lever 122 comprising two ends 188, which may project from the handle 118, but in other embodiments, any of a variety of actuators may be provided. Levers, slide actuators, buttons and the like may have any suitable geometry, and may be shaped or sized to be ergonomic. For example, a slider 119 may be located to be easily accessible as shown in FIG. 1. These actuators may be used to control the use of the retractor cannula device, for example, to control a steering mechanism 120 or steering assembly. Handle actuators may also be used to navigate the tubular body (e.g., by bending or flexing), as well as to control the configuration of the retractor assembly 116. During use, the retractor cannula device 100 may be advanced through the working channel of a trocar or introducer and into the working area. In some embodiments, the working area or space may be created by separating structures or tissue using an atraumatic retractor assembly, either alone or in combination with the steering mechanism 120. The steering mechanism 120 may be configured to provide any of a variety of steering features, including various bending planes, various bending ranges, extension and retraction ranges, and rotations ranges, for example. As mentioned previously, in the embodiment depicted in FIG. 1, the actuator comprises a lever 122 with both ends 188 projecting from the housing 118, but in other embodiments, any of a variety of actuators and actuator configurations may be used, including but not limited to dials, knobs, sliders, buttons and the like, as well as electronic touch controls, for example. In some embodiments, only one end 188 of the lever 122 may project from the housing 118. The controls used to manipulate the steering mechanism 120 may be manually manipulated by the user or by a mechanical control system comprising various motors. In still other embodiments, actuators such as the lever 122 may be omitted and the retractor cannula device 100 may be directly coupled to a motor control system. These and other components of the retractor cannula device 100 are described in greater detail below.

The tubular body 102 may have one or more longitudinal channels spanning at least a portion therethrough. The longitudinal channels may be for housing actuating mechanisms, providing communication between ports at the handle to channels in the retractor assembly, or may be working channels. Working channels may be configured for the delivery of various devices, or example, dissection or biopsy instruments, and/or visualization devices such as an endoscope. One or more working channels may be configured for the delivery of therapeutic agents or fluids for irrigation. The tubular body 102 may have a working channel that is configured for visualization functions, e.g., a visualization channel. Additional types of longitudinal channels and their arrangement will be described in further details below.

As previously described, the retractor cannula device 100 may comprise at least one flexible region 124 which may help the retractor cannula device to maneuver efficiency through tissue and may help the retractor cannula device to be navigated atraumatically. In certain embodiments, the at least one flexible region may be situated distally on the tubular body 102, e.g., proximal to the retractor assembly 116. This may permit the tip, i.e., the distal portion, of the retractor assembly cannula to flex or bend, and may allow for 360 degree rotation around its longitudinal axis. Such a configuration may permit the retractor cannula device to navigate to tortuous regions of the body, and may also allow the device to torsion tissue gripped by the retractor assembly to re-position or remove it.

The retractor assembly 116 may also be used with the retractor cannula device 100 to provide therapy or treatment, and may shield surrounding tissue or provide access for the delivery of additional devices. The retractor assembly 116 may be atraumatic, and may be positioned at the surgical or treatment site in a compact or stowed condition (see, e.g., FIG. 3B) and then deployed as necessary (see e.g., FIG. 3C).

Any suitable atraumatic structure may be used with the distal end 106 of the retractor cannula device 100 to help reduce the risk of inadvertent injury to surrounding structures during a procedure. For example, an atraumatic retractor assembly may be configured to provide tactile feedback, e.g., rigidity, pliability or feel of the tissue or structures in contact with the distal-most portion of the retractor assembly, to the user. In one embodiment, an atraumatic retractor assembly may also provide dissection or retraction capabilities and may be able to displace surrounding tissue without injuring it. Additionally, the overall shape of an atraumatic retractor assembly may allow manipulation of nerves, e.g., nerves in the proximity of an intervertebral disc, as the retractor cannula device is advanced without harming the nerve or causing pain. In one embodiment, a retractor assembly may have a curved shape and no sharp edges, burrs or other features that may pierce, snag, tear or otherwise harm tissue that comes into contact with the retractor assembly. The shape, surface contours and/or overall finish of an atraumatic retractor assembly may be selected to help reduce or minimize impact forces when the tip, i.e., the distal portion of the retractor cannula device, comes into contact with structures such as nerves, muscle and the spinal dura, among others.

The atraumatic element at the distal end 106, e.g., the retractor assembly 116, may also be controllably pivoted or actuated from the closed configuration to the open configuration, or otherwise comprise two or more surfaces or structures that are independently controllable. For example, the retractor assembly 116, which may be urged from a closed configuration to an open configuration to create a working space in the surrounding tissue, which may act as a clearing for improved visibility of any suitable visualization devices provided therein. Once a target tissue is positively or at least sufficiently identified, the retractor cannula device may then be advanced to the target tissue in either the closed or open configuration, as appropriate, to create a first working space. The retractor assembly may then be actuated to the open configuration to create a second working space and so forth to advance the retractor cannula device towards a targeted body region, e.g., to advance the retractor cannula device in a spinal space. In addition, the retractor cannula device may be used to provide saline or another type of cleaning solution or a contrast agent to the working area for enhancing visualization. In certain embodiments, the retractor assembly 116 may be moveable or articulated such that it may be used to displace surrounding tissue or structures. The displacement of tissue or structures may be felt by the user and may provide a more tactile sense of tissue movement or displacement. The tissue displacement may result from active movement of the retractor assembly under control of the user, or movement caused by releasing the retractor assembly from a first biased position to a second position. Other conventional techniques for manipulation of surgical implements may also be used to control the retractor cannula device.

Figure 21A:
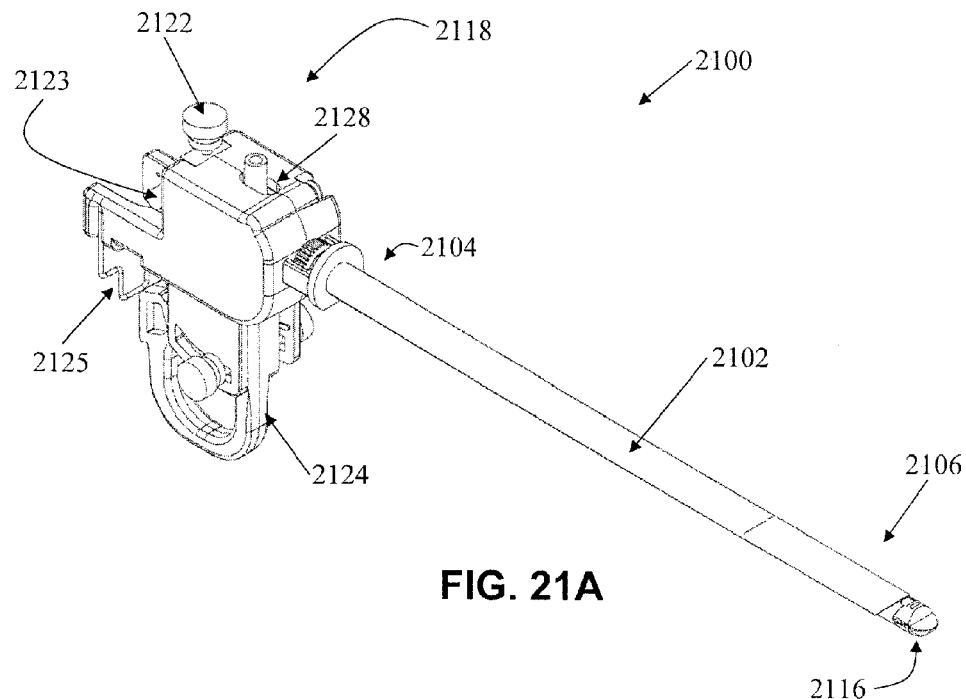
FIGS. 21A and 21B depict a perspective and side view (respectively) of another variation of a retractor cannula device.
Figure 21B:
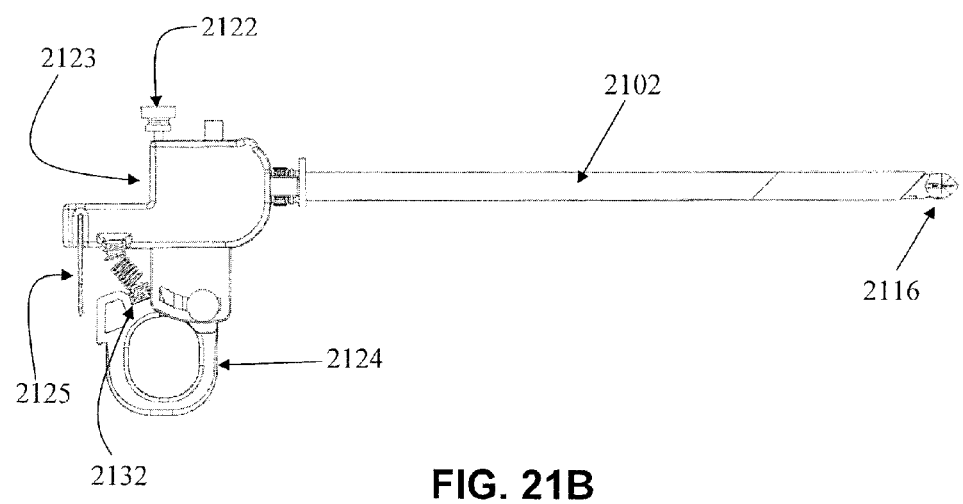

Another variation of a retractor cannula device is shown in FIGS. 21A and 21B. Refractor cannula device 2100 may comprise a tubular body 2102 with a proximal end 2104 and a distal end 2106, a retractor assembly 2116, and a handle 2118. As with the retractor cannula device 100, the proximal end 2104 of the tubular body 2102 may be associated with one or more ports at the handle 2118, for example, handle port 2123 and auxiliary port 2128. The ports and the handle 2118 may be configured to accommodate various devices, for example, a device coupler 2122 may be provided to help attach a device (e.g., an endoscope) to the handle 2118. The handle 2118 may comprise actuators for the navigation and actuation of the distal end 2106 of the tubular body 2102 (e.g., the retractor assembly 2116), such as a pivot lever 2124 which may be configured to control the configuration of the retractor assembly 2116. As shown in FIG. 21B, a spring 2132 may be provided to bias the pivot lever 2124 into a certain configuration. A pivot lever lock 2125 may also be included as desired for restricting the actuation of the pivot lever 2124. Other actuators, such as levers, sliders, buttons, and the like may also be included as appropriate.

The various components of the retractor cannula devices described above may be made from any suitable materials. For example, the tubular body and/or the retractor assembly may be made of a rigid material, such as stainless steel or rigid plastic. The flexible region 124 may be made of any combination of flexible biocompatible polymers or pliable metals. In some embodiments, the flexible region may be actuated by wires or struts within the tubular body, or by sliding other elongate members provided in the tubular body, for example. Alternatively or additionally, the tubular body may be strong and flexible, and may be made of a combination of materials, such as stainless steel metal braid embedded in elastic polymers. Examples of elastic polymers may be (but are not limited to) Pebax, polyurethane, and silicone.

The dimensions of the various components of a retractor cannula device, such as the retractor assembly, flexible region, tubular body, handle, etc., may be sized and selected based on the particular therapy being provided and the targeted body region. For example, one embodiment of the retractor cannula device may have dimensions suitable for navigation to a spinal region for diagnostic evaluation and/or to apply a therapy thereto. In another embodiment, the retractor cannula device may be sized to fit within an epidural space or in proximity to an intervertebral disc. Other embodiments may be configured for use in the chest cavity (e.g. pleural biopsy or pleuracentesis) or abdominal-pelvic cavity (e.g. bladder neck suspension), or for non-spinal procedures such as breast biopsy and transvaginal oocyte retrieval, for example. In some embodiments, the retractor cannula device 100 may have a diameter of about 5 mm or less, while in other embodiments, the retractor cannula device may have a diameter of about 3 mm or less, or even 2.5 mm or less. In another embodiment, one or more of the working channels of the retractor cannula device 100 may have a diameter of about 5 mm or less, about 3 mm or less, about 2 mm or less, about 1 mm or less, or about 0.8 mm or less. Additional details and descriptions of the various components of a retractor cannula device are provided below.

A. Retractor Assembly

The retractor cannula device 100 may be used to manipulate a targeted body region in different ways. For example, the retractor cannula device may be used to dilate and/or displace tissue to create a working space, aspirate and/or irrigate the target tissue, infuse medications, inject substances, remove tissue, etc. Furthermore, the retractor cannula device may be used to deliver a variety of devices to a target tissue, for example, any visualization devices (e.g., endoscope), ablation devices, expandable devices, thermal energy devices, stimulation electrodes, etc. Different retractor assemblies may be used with the retractor cannula device to effect one or more of the above functions. For example, a retractor assembly may have one or more retractor elements, e.g., jaws, and may have one or more configurations for performing different functions, e.g., an open configuration and a closed configuration. By transitioning the retractor assembly from a closed to an open configuration, the retractor elements of a retractor assembly may be urged outwardly against the surrounding tissue to provide a space for direct visualization and/or the insertion of additional devices. In some variations, an atraumatic retractor assembly may cycle between the closed and open configuration to assist in the advancement of the retractor cannula device. In some cases, the operation of the retractor assembly may take place with the assistance of direct visualization, such as images from an endoscope. Some variations of an atraumatic retractor assembly may comprise working channels that are in communication with one or more channels or lumens in a tubular body of a retractor cannula device. Longitudinal lumens or access lumens, e.g., the channels 1326, 1328, and 1330 in FIG. 13A may extend through the length of the tubular body, and may be in communication with the retractor assembly. These channels may be sized to allow passage of the catheters, endoscopes, and instruments/devices, and the like.

The shape and size of a retractor assembly may vary according to the tissue environment (e.g., thin vs. thick tissue, regions of densely packed tissue structures vs. sparsely-distributed tissue structures, volume of liquid media in the vicinity of the target tissue, elasticity of the target tissue, etc.). In some variations, the surface of the retractor assembly may be have one or more curves, where the curvature of the retractor assembly surface (e.g., in the closed configuration) may be uniform around the longitudinal axis of the retractor cannula device, or may be non-uniform around the longitudinal axis. For example, the surface of the retractor assembly may be tapered along a first surface with first angle or slope, and may be tapered along a second surface with a second angle or slope, where the first and second angles or slopes may not be equal. Tapers may have one or more angles or slopes, and curvatures may have one or more radii of curvature. In some variations, the surface of a retractor assembly may have a wider dimension on a first side, and a narrower dimension on a second side. While certain examples of retractor assemblies are described below, with certain shapes and curves, it should be understood that other types of retractor assemblies may be used with a retractor cannula device, and may vary according to the desired functionality as well as the targeted body region or tissue, e.g., have different sizes, different shapes, different curves, and numbers of longitudinal channels, etc.

1. Rounded Retractor Assembly

Figure 3A:
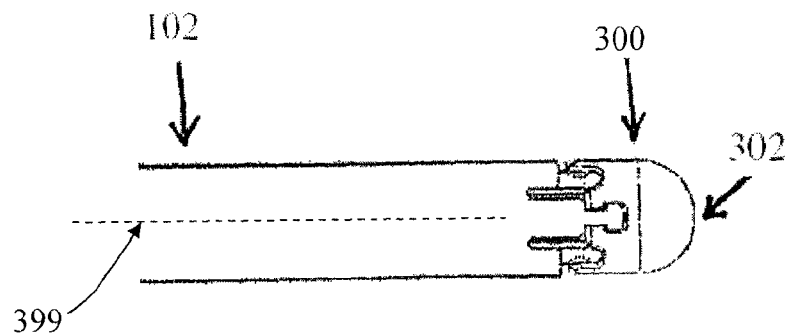
FIG. 3A is a superior view of a distal portion of a retractor cannula device with a rounded retractor assembly.
Figure 3B:
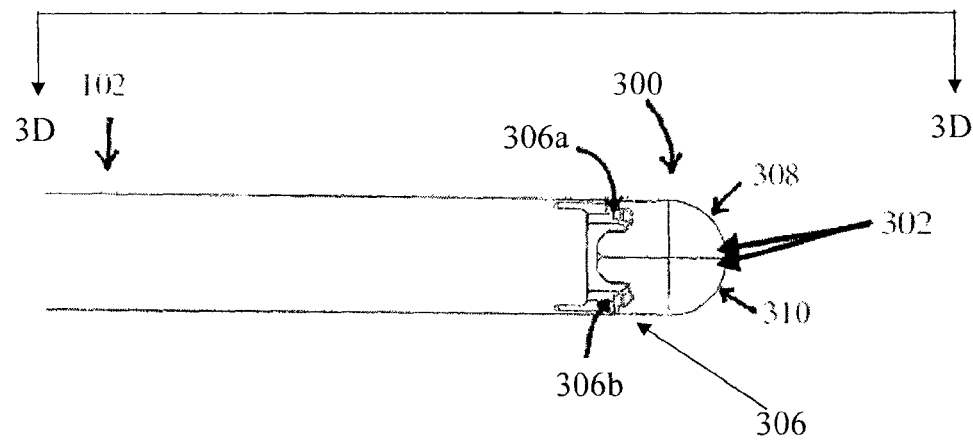
FIGS. 3B and 3C are side views of the distal portion of a retractor cannula device with a rounded retractor assembly in a closed configuration and an open configuration, respectively.
Figure 3C:
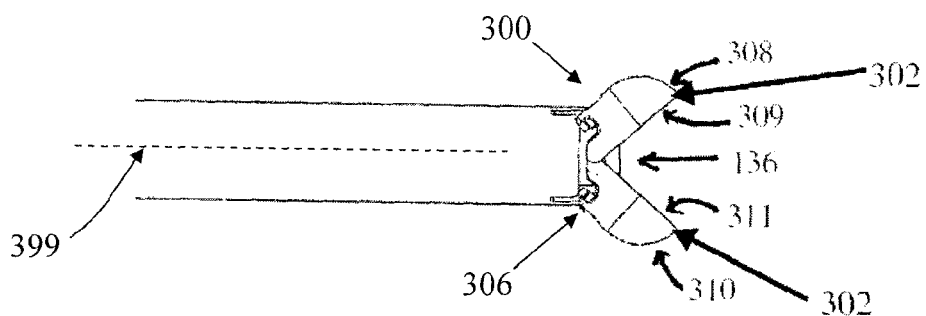
Figure 3D:
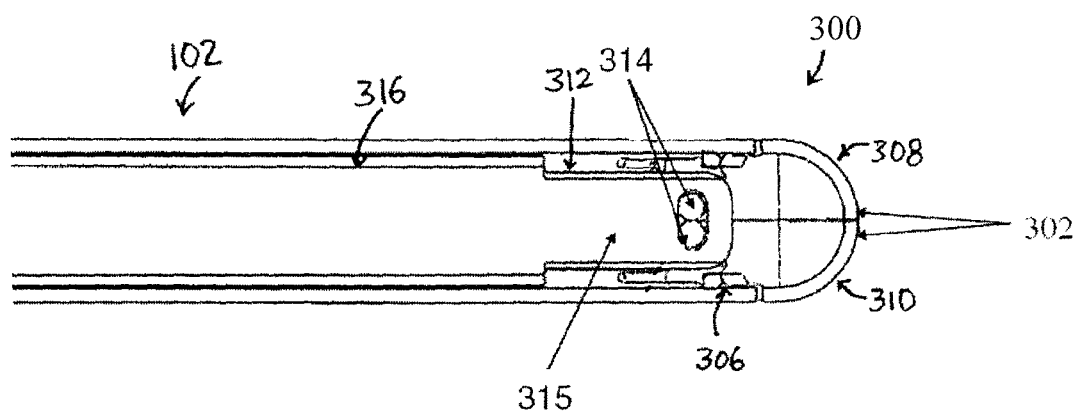
FIG. 3D is a cross-sectional view of the device in FIG. 3B.
Figure 3E:
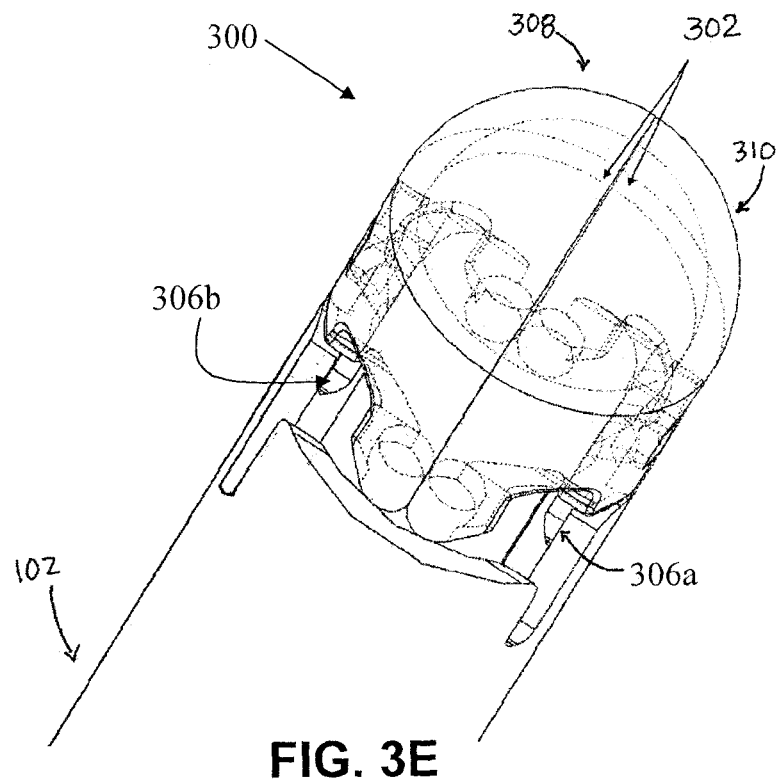
FIG. 3E is a perspective ghosted view of the retractor assembly in FIG. 3A.
Figure 3F:
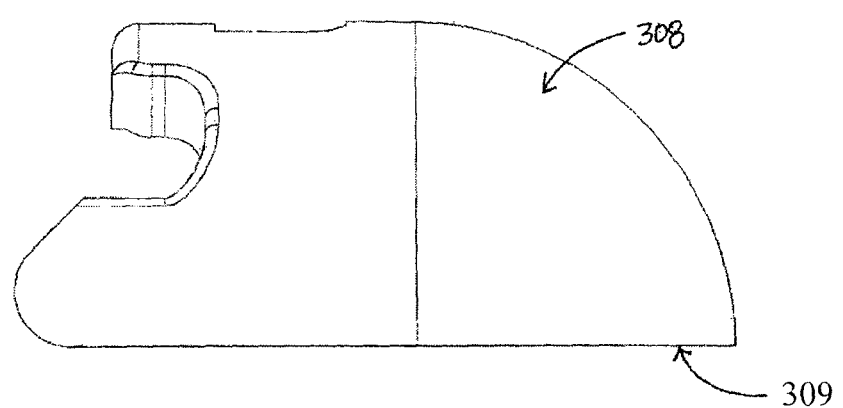
FIG. 3F is a component view of a rounded retractor element.

One embodiment of a retractor assembly is shown in FIGS. 3A to 3F. A superior view of retractor assembly 300 is shown in FIG. 3A, a side view of retractor assembly 300 is shown in FIG. 3B, and a perspective view in FIG. 3E. As depicted there, the retractor assembly 300 comprises two retractor elements, jaws 308 and 310, shaped such that when in the closed configuration, jaws 308 and 310 mate to form a substantially smooth round shape, similar to a bullet, where the curvature of the jaw surfaces is uniform around the midline 399 of the tubular body 102. The surfaces of the jaws 308 and 310 may be symmetrically curved such that they meet at a distal portion 302. Additionally or alternatively, embodiments of a retractor assembly may comprise one or more retractor elements, such as paddles, flaps, lobes, tabs, jaws, and the like. The retractor assembly 300 may have jaws shaped with one or more curved surfaces as described above, such as a sphere, dome, tapered elliptical shape, or any other shape that may help to reduce trauma to surrounding tissue. The rounded retractor assembly is shown in FIGS. 3A and 3B, and each of the jaws 308 and 310 are shaped as a half sphere, as depicted in FIG. 3F. FIG. 3F is an enlarged depiction of jaw 308 with inner edge 309 (jaw 310 and inner edge 311 are mirror reflections of jaw 308 as depicted). Other atraumatic geometries, which are described below, may also be used.

The jaws 308 and 310 may have one or more configurations, for example, a closed configuration (as depicted from the side in FIG. 3B, and in perspective in FIG. 3E), and an open configuration, (as depicted in FIG. 3C). Although the jaws 308 and 310 in FIG. 3B are contacting each other around their outer edges when in the closed configuration, in other examples, the jaws may not fully close. While the jaws 308 and 310 are shown to open and close symmetrically about the midline 399, in other variations of a retractor assembly, the jaws may not move between the open and closed configuration symmetrically. In the open configuration, a working space 136 may be provided between the two jaws 308 and 310. It should be understood that the retractor assembly 300 may comprise more than two jaws, including three or more jaws that may be shaped such that the distal portions 302 of the jaws form a smooth, round, and atraumatic shape in the closed configuration. The jaws 308 and 310 may be coupled to the tubular body 102 using a hinge mechanism 306. Each jaw may be coupled to the tubular body 102 by one or more hinges (306a and 306b) configured in any suitable way to expose or present the working space 136 when transitioned between the closed configuration and the open configuration. In some variations, jaws and any other retractor elements may be coupled to tubular body 102 by pins, mandrels, screws, etc.

In certain embodiments, a hinge mechanism 306 may comprise living hinges and/or mechanical hinges formed by rivets, pins, or screws, for example. The hinge mechanism may be made of any suitable material. In one example shown in FIGS. 3B and 3C, the hinge mechanism 306 comprises hinges 306a and 306b which may lie flush against the outer surface of the tubular body 102. The hinges 306a and 306b may be configured such that when the jaws 308 and 310 are transitioned into the open configuration, as shown in FIG. 3C, one or more distal portions 302 of the jaws 308 and 310 may move away from the other, or move away from the midline 399 of the device, i.e., move away from each other symmetrically, exposing the working space 136. As previously described, the jaws 308 and 310 may move away each other in asymmetrically, i.e., move away from each other from a longitudinal axis that is parallel to the midline 399. In one embodiment, as illustrated in FIG. 3C, the inner edges 309 and 311 of the jaws 308 and 310 form an angle, and in the open configuration, this angle may be about 90 degrees. In other embodiments, the angle formed by the inner edge 309 and the inner edge 311 may be any value from about 1 to about 359 degrees, including about 60 degrees, about 90 degrees, about 120 degrees, about 180 degrees, or 270 degrees. The hinge mechanism 306 of the retractor cannula device may be made of metal or plastic, or other similar suitable materials. In addition to mechanical hinges that comprise a rivet upon which the hinges 306a and 306b rotate, some embodiments may utilize a living hinge. The living hinge may comprise any material that can be fashioned into a thin, flexible strip, which may comprise the same or different material as the instrument shaft, and may be a metal, plastic or other polymer. In some embodiments, other articulations may be used, including ball-and-socket joints. In certain embodiments, the articulation between the tubular body 102 and the jaws 308 and 310 may be configured to be slidable along the tubular body 102 for additional maneuverability. Additionally or alternatively, the entire retractor assembly may be configured to be slidable along the tubular body, with or without jaw angulation. For example, the retractor elements of a retractor assembly may be coupled to a tubular body via a flexible region.

In some variations, when the retractor assembly 300 is in an open configuration, the jaws 308 and 310 are configured to provide a working space that may help to improve the field of view of any visualization instrument that may be used with the retractor cannula device. For example, where a visualization device (e.g., an endoscope) is provided between the jaws 308 and 310 in the proximity of the working space 136, the retractor assembly 300 in an open configuration may provide a forward-looking capability, which may help enhance the visualization and displacing it. This forward-looking capability may be adjusted according to the tissue to be visualized and displaced by varying the angle between the inner edges 309 and 311, adjusting the flexibility of the hinge mechanism 306, and/or varying the size and shape of the jaws 308 and 310, and other related factors.

In some embodiments, the working space 136 is in communication with the tubular body 102. Referring to FIG. 3D, which depicts a cross-section of the retractor assembly 300 along line 3D-3D shown in FIG. 3B, certain embodiments of a retractor cannula device may have an inner shaft 316 within a lumen 312 of the tubular body 102 that may help to support any structures that control and/or navigate the retractor assembly and actuate the jaws 308 and 310. The inner shaft 316 may be axially slidable along the longitudinal axis ($A_L$) to actuate the motion of the jaws 308 and 310, and may be in communication with working space 136. For example, the lumen 312 or the inner shaft 316 may house at least a portion a jaw actuating mechanism. One example of a jaw actuating mechanism is depicted in FIG. 3D. As shown there, the inner shaft 316 comprises a tab 315 that may articulate with pins 314, where the pins 314 may be coupled to the jaws 308 and 310. Sliding of the inner shaft 316 may translate the tab 314, which may rotate the pins 314 so that the jaws 308 and 310 may pivot outwardly (i.e., may move away from the other, or move away from the longitudinal axis ($A_L$) of the device). The inner shaft 316 may be controlled using an actuator on the handle 118, for example, the slider 119. Other embodiments may use other actuating mechanisms, for example pull wires or struts, to open or close the jaws. The pull wires may include metallic or polymeric wires, which may be single-stranded or multi-stranded, and may included twisted or braided members. In still other examples, the movement of the jaws may be asymmetrical (e.g., one jaw may be biased into one position while the other jaw is unbiased, etc.) or one or more jaws may be immovable while one or more other jaws are movable.

2. Tapered Shape Retractor Assembly

Figure 4A:
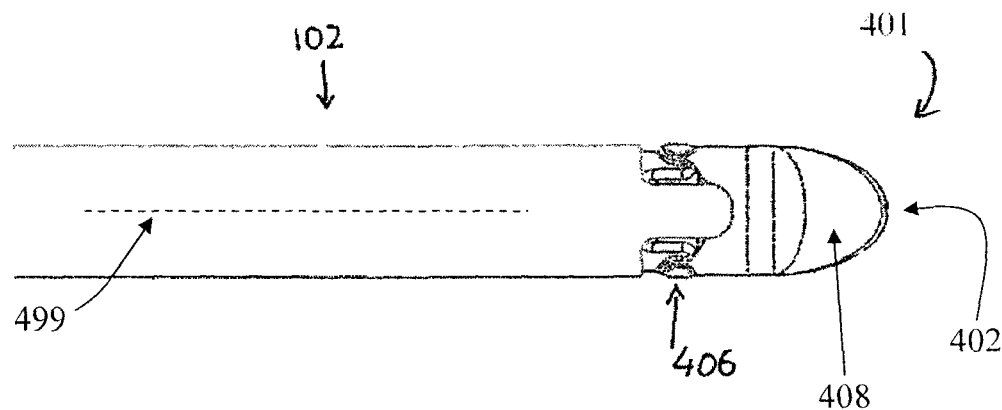
FIGS. 4A to 4F depict an embodiment of a retractor cannula device with a tapered retractor assembly.
Figure 4B:
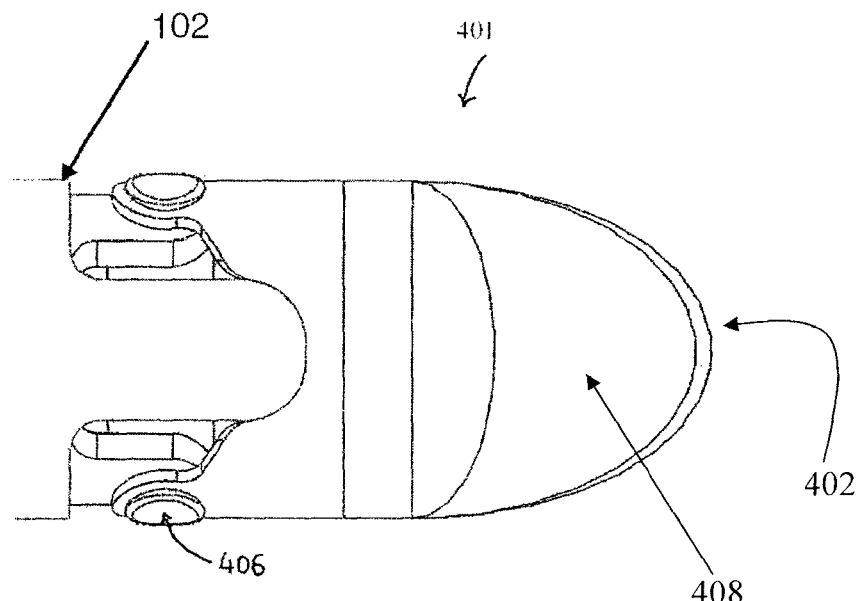
Figure 4C:
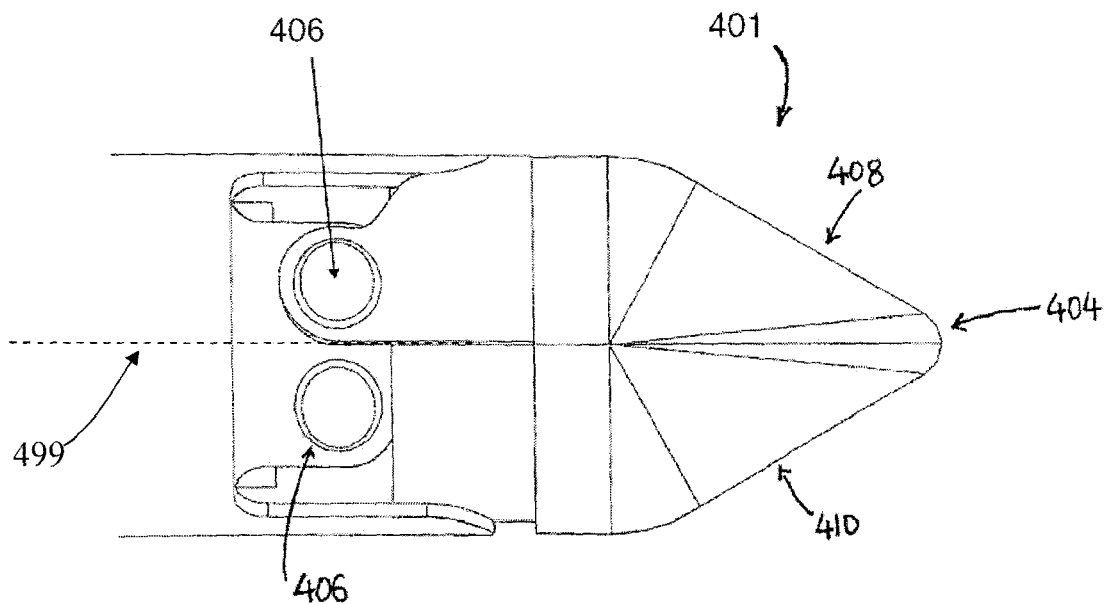

Another embodiment of a retractor assembly 401 is depicted in FIGS. 4A to 4F. The retractor assembly 401 comprises two retractor elements, jaws 408 and 410. Additionally or alternatively, embodiments of a retractor assembly may comprise one or more retractor elements, such as paddles, flaps, lobes, tabs, jaws, and the like. The jaws 408 and 410 have curvatures that are non-uniform around the midline 499. As shown in FIGS. 4A and 4B, the jaw 408 is tapered with one or more slopes or angles along a longitudinal axis, e.g., midline 499. As shown in the superior view in FIG. 4A, the retractor assembly 401 has a first curvature on a first profile of the jaw 408, where the first curvature has a first taper that is generally smooth and rounded towards a distal portion 402, and a second taper that is rounded at a distal portion 402. FIG. 4B is a close-up view that shows where the jaw 408 may be tapered towards a distal portion 402, e.g. the taper of the jaw 408 may be flat proximally and steep distally. FIG. 4C depicts a side view of the retractor assembly 401 that is perpendicular to the views shown in FIGS. 4A and 4B. As shown there, the surface curvature of the jaws 408 and 410 are different from the surface curvature as seen from a superior view of the retractor assembly 401, i.e., the curvature of the jaw surfaces are non-uniform around the midline 499. From the side view, the retractor assembly 401 has a more gradual or uniform taper along a second profile as compared to the first profile shown in FIGS. 4A and 4B. This may be seen also in FIGS. 4E and 4F. While the jaws 408 and 410 have at least two different curved surfaces (e.g., a first tapered surface shown from a superior view, and a second tapered surface shown from a side view perpendicular to the superior view), in other embodiments, the cross-sectional or side profile may be more or less tapered that the taper from the superior profile, where the taper of the jaws 408 and 410 may increase proximally and/or decrease distally. In other embodiments, any tapered or non-tapered configuration may be used. While jaws 408 and 410 may have symmetric tapers on two orthogonal jaw surfaces, other jaw variations may have symmetric tapers on more than two jaw surfaces (which may or may not be orthogonal), and/or may have asymmetric tapers as suitable for atraumatically navigating through the target tissue environment. In this particular example, the jaws 408 and 410 have a cross-sectional profile with an acute angle (see FIG. 4F), where the apices form a flat tapered tip 404 in the closed configuration, as shown in FIG. 4C.

Figure 4D:
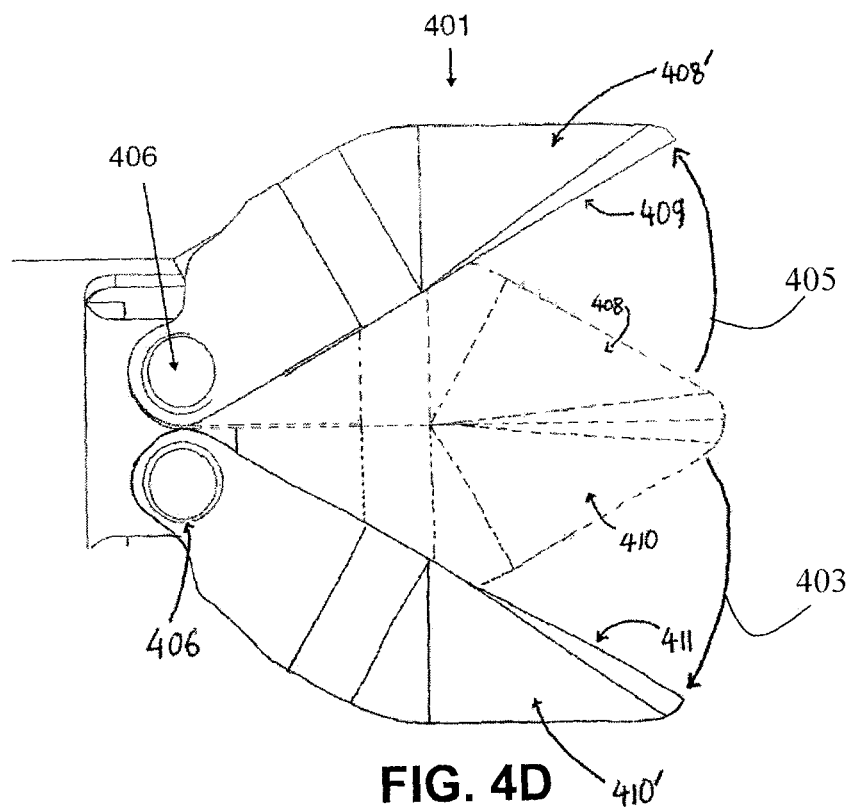

As described with respect to retractor assembly 300, retractor assembly 401 may have the same or similar configurations. The open configuration is illustrated in the solid lines of FIG. 4D, showing the action of the jaws 408 and 410, while the dotted lines represent the location of the jaws 408 and 410 in the closed configuration. The jaws may be urged into the open configuration by a rotating hinge 406 in the direction of arrows 405 and 403, where an angle is created between the edges 409 and 411, and the jaws assume the open configuration. In the open configuration, the angle between edges 409 and 411 may be any value from about 0 degrees to about 270 degrees or more, including up to about 30 degrees, about 60 degrees, about 90 degrees, about 120 degrees, about 180 degrees, about 270 degrees, or more. As mentioned previously, in some embodiments, both jaws 408 and 410 need not open or close symmetrically, and in some embodiments, one or both jaws may even have a fixed location relative to the tubular member 102. The actuating mechanism of the retractor assembly 401 may be the same or different from the actuating mechanisms disclosed for the retractor assembly as previously described and depicted in FIG. 3D. Hinge mechanisms, configurations, functions, and their actuation have been described and shown previously, e.g., in FIG. 3D.

3. Angled Retractor Assembly

Figure 22A:
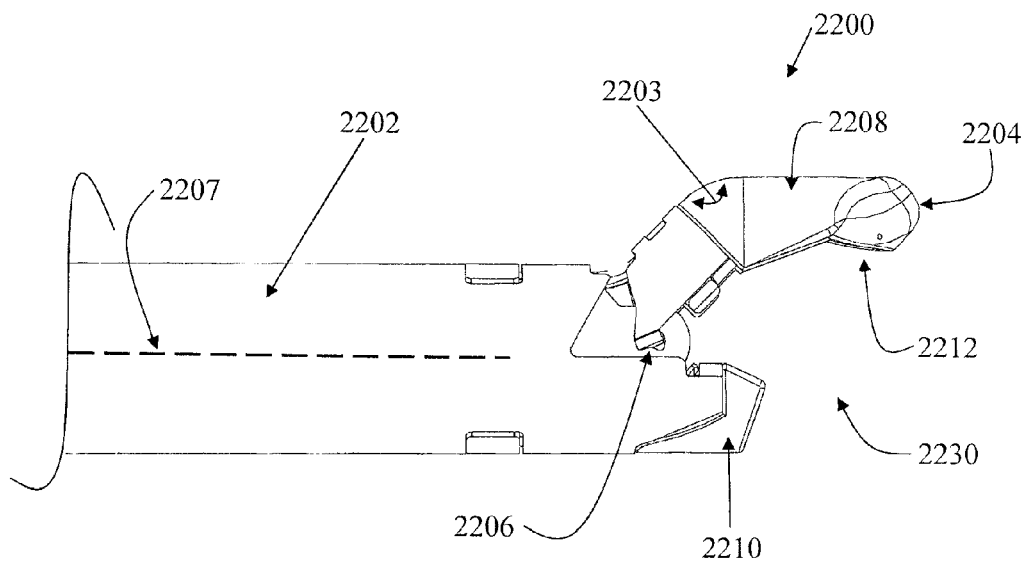
FIG. 22A is a side view of a distal portion of a retractor cannula device with an angled retractor assembly.
Figure 22B:
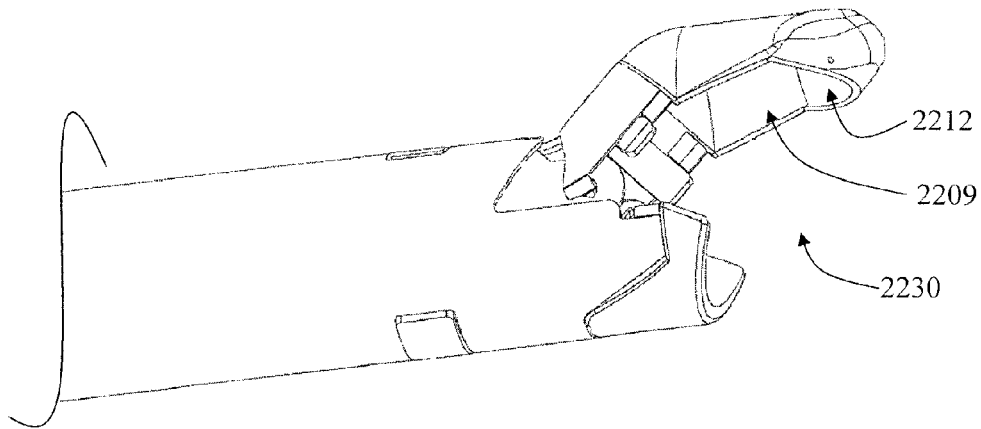
FIG. 22B is a first perspective view of the angled retractor assembly from FIG. 22A.
Figure 22C:
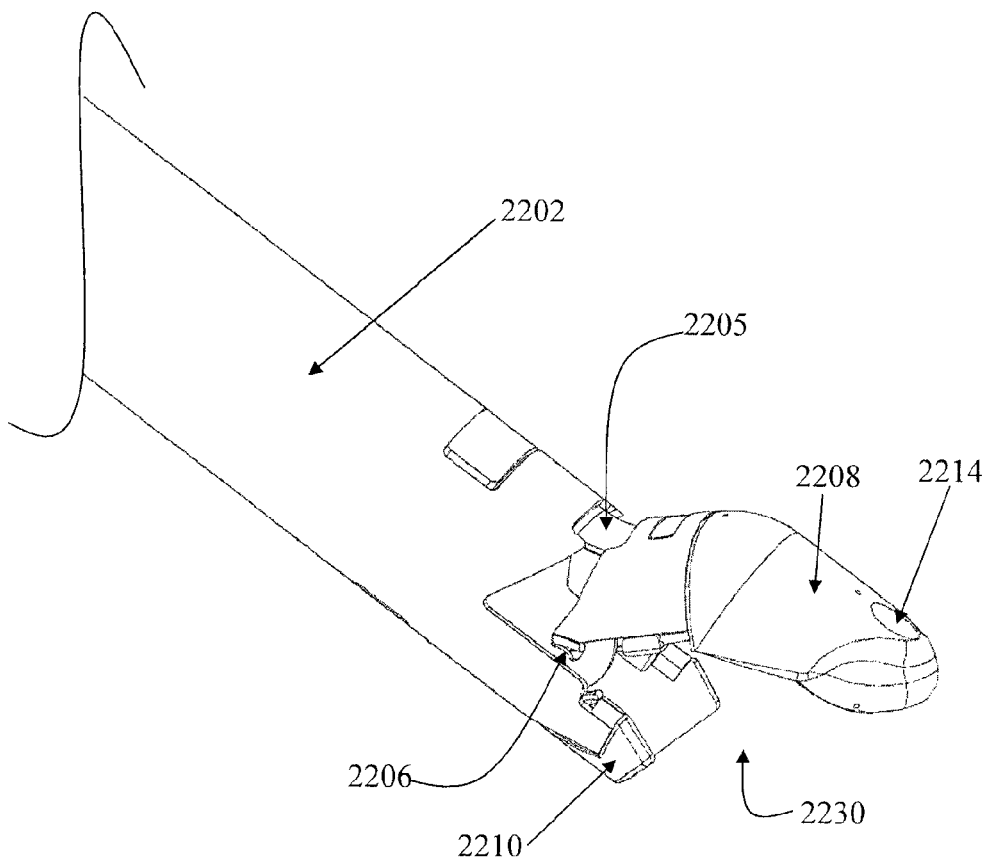
FIG. 22C is a second perspective view of the same angled retractor assembly.

In certain embodiments of a retractor assembly, the jaws may not be symmetric about a midline of the device in shape or movement. FIGS. 22A-22C depict an angled retractor assembly 2200 in an open configuration, where the angled retractor assembly 2200 comprises a first jaw 2208 that has an angle 2203, and a second jaw 2210 that does not have an angle. In some embodiments, the second jaw 2210 may be optional. The first jaw 2208 may comprise a rounded tip 2204, where the shape of the rounded tip 2204 is such that a rounded tip cavity 2212 is provided therein. The angle 2203 may have any angle between 1 degree and 180 degrees, for example, from about 150 degrees to about 179 degrees, or from about 100 degrees to about 130 degrees, or about 120 degrees to about 160 degrees, or from about 90 degrees to about 120 degrees. As indicated previously, the angled retractor assembly 2200 is shown here in its open configuration. When actuated to its closed configuration, at least a portion of the first jaw 2208, e.g., the rounded tip 2204, may extend beyond the midline 2207. This may help the retractor assembly 2200 to grasp and/or hook tissue in the rounded tip 2204. The degree to which tissue is engaged may be adjusted by varying the angle 2203, along with other features, as will be described below. In some variations, the extension of the first jaw 2208 beyond the midline 2207 may not enclose the retractor assembly 2200, where even in the closed configuration, fluids or devices in the one or more lumens of the tubular body 2202 may still exit the retractor assembly 2200. For example, in the closed configuration, the first jaw 2208 and the second jaw 2210 may form a side aperture, and in variations with a single jaw, the jaw 2209 may form a side aperture with the tubular body 2202. The shape of the first jaw 2208 is such that a first jaw cavity 2209 is contained therein, and as depicted in FIG. 22B, the first jaw cavity 2209 and the rounded tip cavity 2212 may be in communication with each other. The rounded tip 2204 may also have a rounded tip hole 2214, as seen in FIG. 22C, that may be used to infuse a flush solution or contrast agent. The working space 2230 may be generally defined as the region between the first jaw 2208 and the second jaw 2210, and may include the rounded tip cavity 2212 and the first jaw cavity 2209, as well as any additional space created by the retractor assembly 2200 as it dilates tissue.

As with the other retractor assembly embodiments, the first jaw 2208 may be attached to the tubular body 2202 by a hinge 2206 on the side, as well was a secondary hinge 2205 on the top, as depicted in FIG. 22C. In some variations, the hinge 2206 may be a mechanical hinge, e.g., a pin, screw, a rotatable member, and the like, and the secondary hinge 2205 may be a living hinge that may bend, but not rotate. In general, any suitable hinge mechanisms may be used that allow the retractor assembly 2200 to open, close, and bend as desired. While second jaw 2210 as shown in FIGS. 22A-22C is shown to be fixedly coupled to the tubular body 2202, in other embodiments it may also be coupled to the tubular body 2202 by a hinge mechanism. Second jaw 2210 may be significantly shorter in length than first jaw 2208, but in other variations, the size of each of the jaws with respect to each other may be varied according to the desired level of tissue grasping, dilating, and manipulating. In some embodiments, the first jaw 2208 and the second jaw 2210 may be made of a clear material, i.e., optically transparent, so that even in the closed configuration, a visualization device (e.g., an endoscope) contained therein may still be able to acquire images. The first jaw 2208 and the second jaw 2210 may comprise additional features and have additional or different configurations, as will be described later on.

In other embodiments of a retractor assembly, the retractor assembly may be an extendable structure, where the extendable structure may be provided with one or more support elements. The support elements may be oriented longitudinally, radially, and/or circumferentially along the retractor assembly jaws to support the various configurations the jaws may take on. The configuration of a support element may be complementary to the shape or configuration of the retractor assembly. In one embodiment, the support element may comprise a helical configuration, for example. In some embodiments, the support elements may be located about a tubular body lumen (e.g., lumen 312). The support elements may comprise any of a variety of materials, including but not limited to a metal and/or polymeric material. The support element maybe rigid, semi-rigid or flexible, and at least a portion of the support element may be attached or coupled to the shaft, the inner or outer surface of the retractor assembly, and/or embedded in the inner edges of the retractor assembly.

4. Retractor Assembly Configurations and Mechanisms

As described above, retractor assemblies may have one or more retractor elements, for example, jaws, that may assume any size or geometry as appropriate for atraumatic manipulation of and navigation through tissue. While examples of mechanisms for actuating a retractor assembly have been described above, other mechanisms may be used to position the retractor assembly in a variety of configurations for various functions. In certain embodiments, a mechanism that actuates a retractor assembly may be biased towards one configuration or the other, or to a third configuration. For example, the jaws or retractor elements may be biased towards a closed configuration, such that in the absence of an actuating force, the retractor assembly remains in the closed configuration, and assumes the open configuration when it is actuated. A retractor assembly with a bias towards the closed configuration may be used to manipulate and/or grab tissue, for example, for removal or replacement. In other embodiments, the retractor members may be biased towards an open configuration, such that in the absence of an actuating force, the retractor assembly remains in the open configuration, and assumes the closed configuration when actuated. A retractor assembly with a bias towards the open configuration may be used, for example, as a dilator or displace tissues or structures. A variety of bias mechanisms may be utilized as common in the art, for example, a spring may be used to maintain the retractor member(s) in a particular configuration (e.g., the bias spring 2132 shown in FIG. 21B), but forces may be applied to overcome the spring force and to transition the retractor member(s) to an alternate configuration. The spring or other bias member may act directly on one or more jaw members, or may act on the actuator located in the proximal housing of the device. Of course, certain embodiments may lack a bias to a configuration. In some embodiments, the retractor assembly may be releasably lockable into one or more configurations. For example, the jaws may be lockable in a variety of angled positions between their inner edges, from about 0 to about 180 degrees or more, including but not limited to about 60, about 90, about 120, about 180, or about 270 degrees. The movement range of each retractor member may be the same or different. In certain examples of retractor assemblies, one or more retractor elements may have a fixed position, while one or more other retractor elements may be movable. For example, in reference to FIG. 4D, both the jaws 408 and 410 are movable or pivotable to create an angle between the inner edges, however it should be understood that in other embodiments, either jaw may have a fixed position, while the other jaw is movable. In reference to FIG. 22A, the jaw 2210 may be fixed in a given location, and the jaw 2208 may be pivoted about the hinge 2206 to obtain a desired configuration.

Figure 5A:
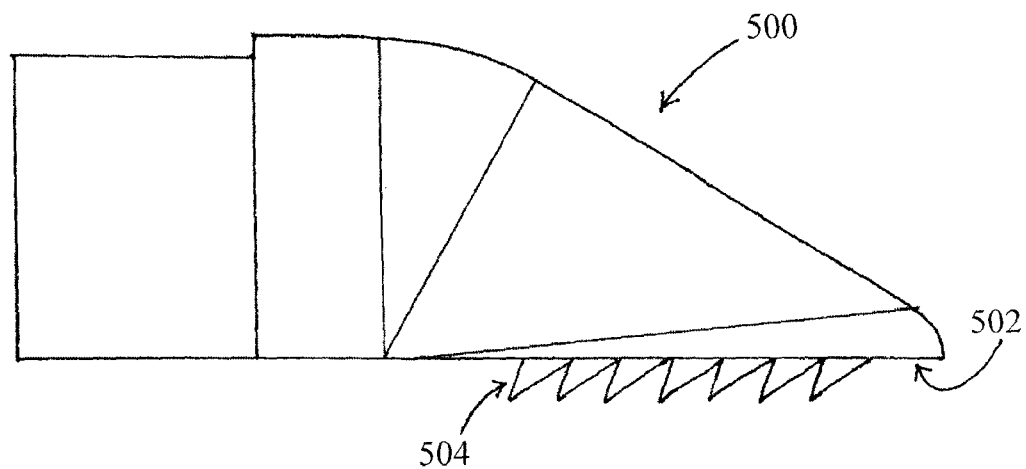
FIG. 5A is a side view of an embodiment of a retractor element comprising tissue-engaging members.
Figure 5B:
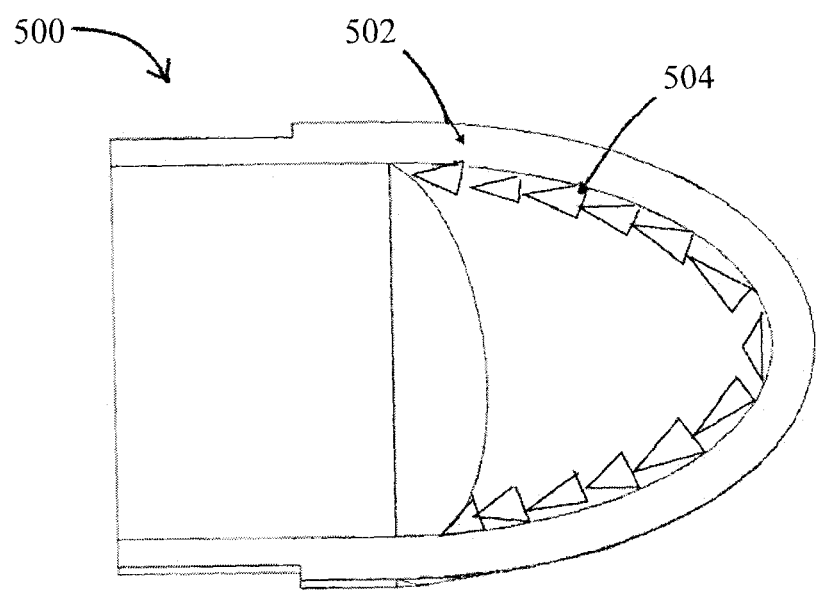
FIG. 5B is an inferior view of the retractor element in FIG. 5A.

The working space provided by the retractor assembly may be characterized with respect to the geometry and configuration of the retractor elements, e.g., jaws. In certain embodiments, the working space may be characterized as the aggregate space directly between any two regions of different retractor elements. The working space may vary depending upon the particular configuration of the retractor elements. In some embodiments, the retractor assembly may characterized by the maximum working space achievable by the retractor assembly within its movement range, where the maximum working space may provide a forward-looking capability that may help to enhance visualization and displacement of tissues. The actual working space and/or maximum working space of an instrument may be restricted or limited by the surrounding tissues or structures. One of skill in the art will understand that the working space or the maximum working space may or may not correlate with the maximum viewing ability provided the retractor assembly. For example, the working space when the jaws are about 180 degrees apart may be low, but the position of the jaws may substantially displace greater amounts of tissue away from the endoscope tip than the jaw angle which provides the maximum working space. Thus, in some instances, the effective viewing space may be bordered by the displaced and undisplaced tissues surrounding the distal end of the cannula device. In some embodiments, it should be understood that the working space may vary with the geometry of the retractor assembly, for example, retractor assemblies with an elongate and/or tapered or rounded jaw configuration may dilate tissue more than retractor assemblies with a shorter jaw configuration. In some embodiments, the inner edges of the jaws may comprise a smooth, rounded surface, which may help reduce the risk of inadvertent snagging of tissue by the retractor assembly. In certain embodiments of retractor elements, the inner edge of the retractor elements may be configured with a variety of tissue-engaging members. Tissue-engaging members may be useful for dissecting and/or removing a portion of target tissue, for example, during the repair of intervertebral discs or for tissue biopsy. In other embodiments, inner edges of the jaws may have tissue-engaging members, where the tissue-engaging members may not be smooth, for example, tissue-engaging members may be hooks, claws, graspers, teeth, and the like. One example of tissue-engaging members that may be used with a retractor assembly, e.g., retractor assemblies 300 or 401, is shown in FIGS. 5A and 5B. As depicted there, the inner edge 502 of retractor assembly jaw 500 may be provided with tissue-engaging teeth 504. The location and orientation of the teeth 504 in the inner edge 502 may help to reduce the risk of inadvertent tissue snagging while actuating jaw(s) 500 for the displacement and/or dilation of tissue. The jaw 500 may be used to engage tissue (e.g., for removal, dissection, biopsy, and the like) using teeth 504. The use of the teeth 504 may be controlled by one or more buttons, slide actuators, dials, levers, etc. of the handle 118, as described previously. While one example of tissue-engaging members are illustrated in FIGS. 5A and 5B, in other examples, tissue-engaging member may have different geometries and arrangements as appropriate for engaging the target tissue. In certain embodiments, as shown in FIGS. 5A and 5B, the teeth 504 may be angled with sharp/blunt vertices, as shown in FIG. 5A, but may be of any suitable geometry, e.g., domed, trapezoidal, helical, and the like. Also, the teeth 504 may be uniformly set at a slant with respect to the inner edge 502 to optimally secure tissue after initial contact, but it should be understood that tissue-engaging members may be set in alternate conformations, for example, tissue-engaging members may be non-uniformly set with different slants or no slants, and the tissue-engaging members may be of non-uniform shapes. The degree to which the teeth 504 extend beyond the inner edge 502 may vary, with some extending beyond the edge 502 as shown in FIG. 5A, but in other embodiments, tissue-engaging members may not protrude or extend beyond the edge 502. The tissue-engaging members on the inner edge of the retractor elements may be set a suitable distance away from the edge to limit trauma to surrounding tissue during the navigation of the retractor cannula device towards the target body region. In some embodiments, the tissue-engaging members on the inner edge are set approximately about 0.1 mm to about 1 mm or more away from the inner edge 502 of jaw 500. In some embodiments, tissue-engaging members, e.g., teeth 504, may be arranged along the perimeter of inner edge 502, as depicted in FIG. 5B which shows a bottom view of jaw 408. As shown there, teeth 504 may be arranged to tile a portion of the inner cavity of the jaw. It should be understood that any arrangement, and any density (which may or may not be homogeneous in the entire inner edge 502) of tissue-engaging members may be used in the inner edge. The teeth 504 may be made of the same material as the jaw 500, but may also be made of different materials. Additionally or alternatively, other surface enhancements and coatings may be applied to the inner edge of the retractor elements and/or protrusions, such as hydrophilic or hydrophobic materials.

In some embodiments, the retractor elements and any tissue-engaging members provided in their inner edge, may be made of any transparent polymer, such as (but not limited to) polyester copolymers (PETG, PETE), nylon, urethane, polycarbonate, acrylic, and/or silicone. In some embodiments, the retractor elements may be made of an opaque material. Alternatively or additionally, the retractor elements may have a metal frame which may then be covered with one or more of the aforementioned polymers. The frame may be made of (but not limited to) stainless steel, titanium alloy, cobalt chromium, tungsten, tantalum. In certain embodiments, at least a portion of the retractor elements may be made of glass. Alternatively or additionally, the retractor elements may be constructed of radio opaque materials to allow visualization of the distal tip of tubular body 102 in X-ray imaging. In other embodiments, the retractor elements include a marker or other feature(s) making all or a portion of the retractor elements perceptible using external imaging modalities. In another embodiment, the marker or feature is a radio opaque marker. Alternatively or additionally, the retractor elements may be constructed of materials that are readily resolved by ultrasound or other imaging modalities. In some embodiments, some portion of the jaw (e.g. distal/forward-looking portion) may be made of a soft material to minimize trauma to surrounding tissue.

Figure 4E:
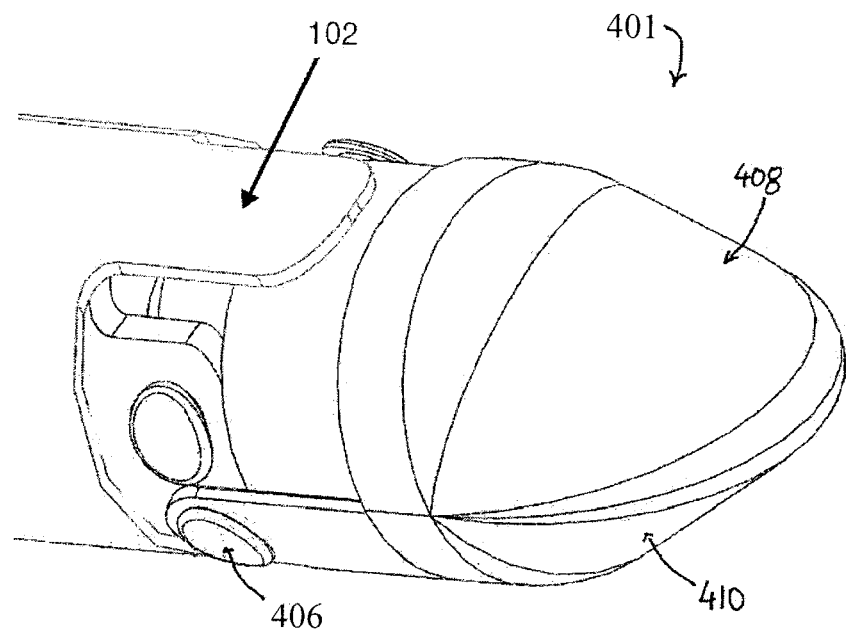
Figure 4F:
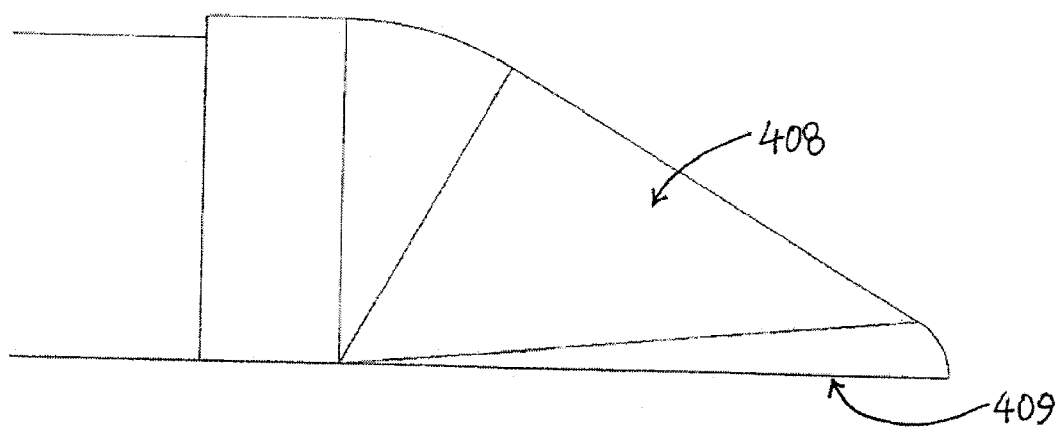

The distal portion of retractor elements, e.g., jaws as shown in FIGS. 3E and 4E, may be selected from a material that is transparent, which may be desirable for the operation of the port components, such as for visualization devices. In some embodiments, the retractor assembly may be formed from rigid, clear plastic, while in other embodiments, the retractor assembly may comprise a flexible, deformable material. In some embodiments, the retractor assembly comprises an opaque material, but in other embodiments may be translucent or transparent, which may facilitate the visualization of the tissue or structures adjacent the retractor assembly. The distal portion of the retractor assembly material may be stainless steel, cobalt chromium, titanium, nickel-titanium, polycarbonate, acrylic, nylon, PEEK, PEK, PEKK, PEKEK, PEI, PES, FEP, PTFE, polyurethane, polyester, polyethylene, polyolefin, polypropylene, glass, diamond, quartz, or combination thereof, for example. In some embodiments, the retractor assembly materials may include the addition of one or more radiographic markers or materials.

Although the retractor assemblies 300 and 401 may be generally symmetrical about the longitudinal axis of the tubular body 102, in other embodiments, the retractor assembly may be asymmetrical, such as retractor assembly 2200. Other retractor assembly jaw configurations may also be used, and slits or windows may be optionally provided to increase direct visualization. For example, the retractor assembly configuration may be altered using different jaw shapes, variable wall thickness and/or by pre-forming curves or fold along one or more regions of the jaw material. In certain embodiments, the retractor assembly may have small apertures, such as slits, near the distal tip to allow for irrigation or administration of therapeutic agents to the target site. As such, the retractor assembly at the distal-most portion of the retractor cannula device may vary in structure and size. In some variations, a retractor assembly may be sized and shaped to help reduce unintended trauma to the target tissue.

As described previously, the jaws of a retractor assembly may be actuated using levers, slide actuators, buttons, etc. provided at a handle, e.g., handle 118. In some variations of a retractor cannula device, the retractor assembly may be steerable, and the retractor cannula device may be maneuvered using a steering mechanism, e.g. steering mechanism 120, to navigate through and/or manipulate tissue. For example, the retractor assembly may be in a closed configuration to facilitate insertion of the retractor cannula device through folds of tissue, and may be opened to create a space between the folds of tissue. In some variations, a practitioner may advance the retractor cannula device under direct visualization to manipulate, dilate, and/or displace surrounding tissue to create a working space in a tissue region. As the retractor assembly of the retractor cannula device expands its jaws from a closed to open configuration, a working space or opening may be created in the surrounding tissue, thereby easing the advancement or atraumatic maneuverability of the retractor cannula device. Thereafter, the atraumatic retractor assembly may be deployed or otherwise used to deform surrounding tissue and/or to make space available (e.g., by displacing or dilating the surrounding tissue) for the retractor cannula device or other treatment device provided by one or more working channels in a tubular body. It is contemplated that one or more of these methods may be used in combination to manipulate the surrounding tissue. Any of a variety of other methods for utilizing the retractor cannula device are also contemplated, some examples of which are described below.

Embodiments of a retractor cannula device may navigate through and manipulate tissue under direct visualization, which may help to facilitate the positioning of an instrument in a targeted area. In some retractor cannula devices, a visualization channel may be provided to accommodate any suitable/appropriate imaging devices, e.g., endoscope. For example, the instrument may be steered using information, such imaging or physiological information, provided by the instrument. The image may come from a fiber optic line or bundle, or a data device such as a camera placed on the distal end of the instrument, or from a sensor or combination of sensors. In one embodiment, the sensor utilizes light to generate the image. In another embodiment, the sensor is adapted to see through the bloody field as presented in the spinal region by selecting at least one infrared wavelength transparent to blood or other bodily fluids. In some embodiments, at least one infrared wavelength transparent to blood presented in the spinal field may have a wavelength of about 1 micron to about 15 microns. In another embodiment, the at least one infrared wavelength transparent to blood presented in the spinal field has a wavelength between about 1.5 micron to about 6 microns. In yet another embodiment, the at least one infrared wavelength transparent to blood presented in the spinal field has a wavelength between about 6 microns to about 15 microns. In yet another embodiment, the at least one infrared wavelength transparent to blood presented in the spinal field has a wavelength between about 1.0 microns to about 1.5 microns, about 1.5 microns to about 1.9 microns, about 2.0 microns to about 2.4 microns, about 3.7 microns to about 4.3 microns, or about 4.6 microns to about 5.4 microns. In yet another embodiment, the wavelength is selected or adapted for use in distinguishing nervous tissue from surrounding tissue and/or minimally vascularized nervous tissue. In yet another embodiment, the wavelength is selected to distinguish nervous tissue from muscle. Wavelength selection information and characterization and other details related to infrared endoscopy are found in U.S. Pat. No. 6,178,346; US Patent Application Publication No. 2005/0014995, and US Patent Application Publication No. 2005/0020914, each of which is hereby incorporated by reference in its entirety.

5. Steering Mechanisms

As mentioned previously, one or more embodiments of the retractor cannula device may be provided with any of a wide variety of steering configurations, such as the steering mechanism 120 depicted in FIG. 1. In one embodiment, the retractor cannula device is steerable in one or more axes, including a device with two axes. In some embodiments, one axis may be a rotation axis. In another embodiment, the retractor cannula device is non-steerable. In yet another alternative embodiment, the retractor cannula device may be pre-formed into a shape that is adapted to access a portion of the spinal region or other region of the body. The shape may include any of a variety of angled and/or curved segments to access a particular body site. In yet another embodiment, the retractor cannula device is situated within the trocar in such a way that the retractor cannula may have steering capability up to about 360° inside the spinal space. A steering mechanism, e.g., the steering mechanism 120, may include one or more flexible bodies or the flexible region 124 on the retractor cannula device 100. The flexible body may be bent by manipulating a control such as the lever 122 located on the housing 118. Various examples of the steering mechanism and the bending region 124 and are described in greater detail below.

B. Tubular Body

1. Flexible Region

As described previously, retractor assemblies may be coupled with a tubular body, where the tubular body may be used to control the positioning of the retractor assembly in a targeted body region. A tubular body may comprise certain features that allow the retractor cannula device to maneuver in anatomically dense regions of the body, where tissue structures tend to collapse around any instrument or device inserted therein, e.g., an intervertbral disc, epidural area. Retractor assemblies, for example, retractor assemblies 300 and 401 as described above, may be directly coupled to a tubular body, e.g., tubular body 102, which may be controlled by a steering mechanism 120, as shown in FIGS. 1 and 2. As depicted there, the tubular body 102 comprises the flexible region 124. In some embodiments, a retractor assembly may be may be coupled to tubular body 102 by a separate flexible component. The bending range of a tubular body may vary depending upon the particular design. The retractor cannula device may be configured with a one-sided or a two-sided bending range with respect to the neutral position of the tubular shaft. The bending range may be from about 0 degrees to about 135 degrees, while in other embodiments, the bending range may be from about 0 degrees to about 90 degrees, and sometimes about 0 degrees to about 45 degrees, and still other times about 0 degrees to about 15 or about 20 degrees. The bending range of the other side, if any, may be less than, equal to, or greater than the first side. In some embodiments, increased bending angles may cause creasing or telescoping of the tubular shaft, which may obstruct one or more channels within the tubular shaft.

Figure 6:
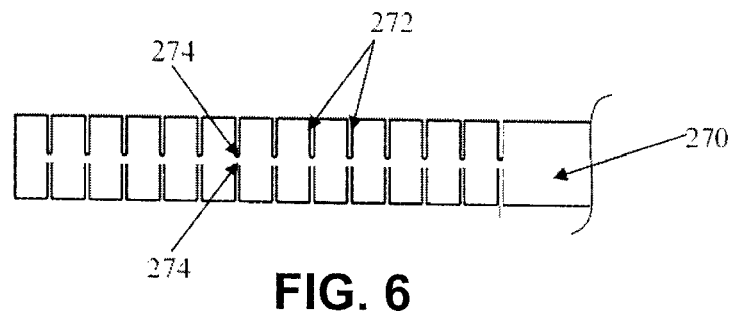
FIG. 6 depicts one embodiment of a flexible region of a retractor cannula device.

In some embodiments, to enhance the bending range of the tubular body, one or more flexion slots may be provided on the tubular body. FIG. 6 depicts one embodiment of tubular body 270, comprising a plurality of slots 272. The slots 272 may have a generally circumferential orientation, but may alternatively have a helical orientation or other orientation. The slots 272 may be equally or unequally spaced along the longitudinal length of the tubular body 270. In one example, the slots that are located about the ends of the flexible region may be spaced farther apart than the slots located about the middle of the flexible region. The slots 272 may have a similar configuration or a heterogeneous configuration. The slots 272 depicted in FIG. 6 also have a generally constant width, but in other embodiments, the width may vary along the length of the slot. The spacing between the slots ends 274 of a slot 272 may be substantially similar or different among the slots 272 comprising the flexible region.

Figure 7A:
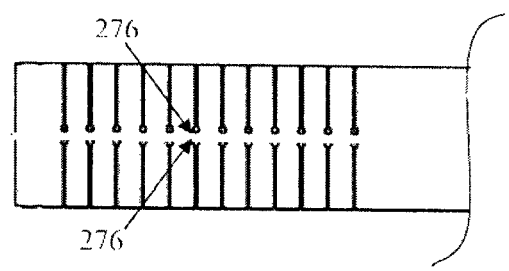
FIG. 7A depicts another embodiment of a flexible region of a retractor cannula device.
Figure 7B:
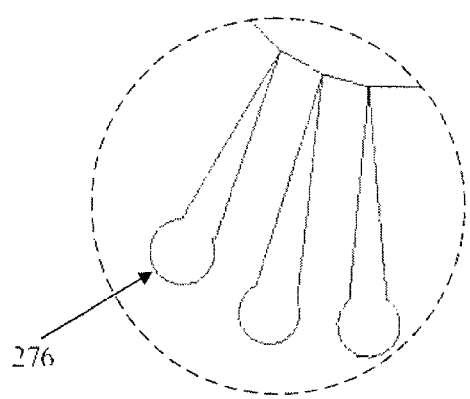
FIG. 7B is a detailed schematic view of the flexible region of FIG. 7A during flexion.
Figure 8:
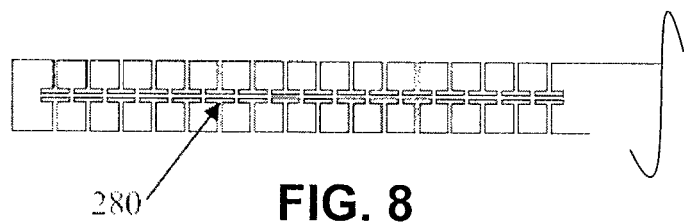
FIG. 8 depicts another embodiment of a flexible region of a retractor cannula device.

As noted in FIG. 6, the slot ends may comprise a rounded configuration, or any other configuration, including but not limited to an oval end, square end, triangular end, or any other polygonal shape for example. In some embodiments, such as the example depicted in FIG. 7A, the rounded ends 276 may have a larger transverse dimension than the width of the rest of the slot 278. In some embodiments, a rounded end may better distribute the flexion stress along the edges of the slot compared to squared or angled ends. Also, ends that are larger than the slots, such as the enlarged rounded ends 276 in FIG. 7A, may reduce the degree of compression or contact between the slot edges during flexion, which may also reduce the risk of cracking at the slot end. FIG. 7B depicts the enlarged rounded slot ends 276 of FIG. 7A in flexion. In some embodiments, the slot end may have a more complex configuration, such as the T-shaped slot end 280 as depicted in FIG. 8.

In some embodiments, the number of slots per slot region may be anywhere from about 1 slot to about 100 slots or more, sometimes about 12 slots to about 50 slots, and other times about 24 slots to about 48 slots. In some embodiments, the length of the flexible region may be anywhere from about 1 inch to about 20 inches, sometimes from about 4 inches to about 10 inches, and other times about 5 inches to about 8 inches in length. In some embodiments, the outer diameter of the flexible region may be about 0.05 inches to about 0.3 inches, sometimes about 0.08 inches to about 0.15 inches, and other times about 0.1 inches to about 0.12 inches. The wall thickness of the flexible region may be in the range of about 0.001 inches to about 0.01 inches, sometimes about 0.002 inches to about 0.006 inches, and other times about 0.003 inches to about 0.004 inches. The slots 272 may have an average slot width in the range of about 0.004 inches to about 0.02 inches, some times in the range of about 0.005 inches to about 0.015 inches, and other times about 0.006 inches to about 0.008 inches. The spacing between the slots 272 may be in the range of about 0.015 inches to about 0.1 inches, sometimes about 0.020 inches to about 0.050 inches, and other times about 0.025 inches to about 0.04 inches. The spacing between the ends of the slots may be in the range of about 0.004 inches to about 0.05 inches, sometimes about 0.006 inches to about 0.02 inches, and other times about 0.004 inches to about 0.01 inches. The maximum transverse dimension of a slot end may be in the range of about 0.004 inches to about 0.008 inches, other times about 0.004 inches to about 0.03 inches, and other times about 0.01 inches to about 0.04 inches.

Figure 9:
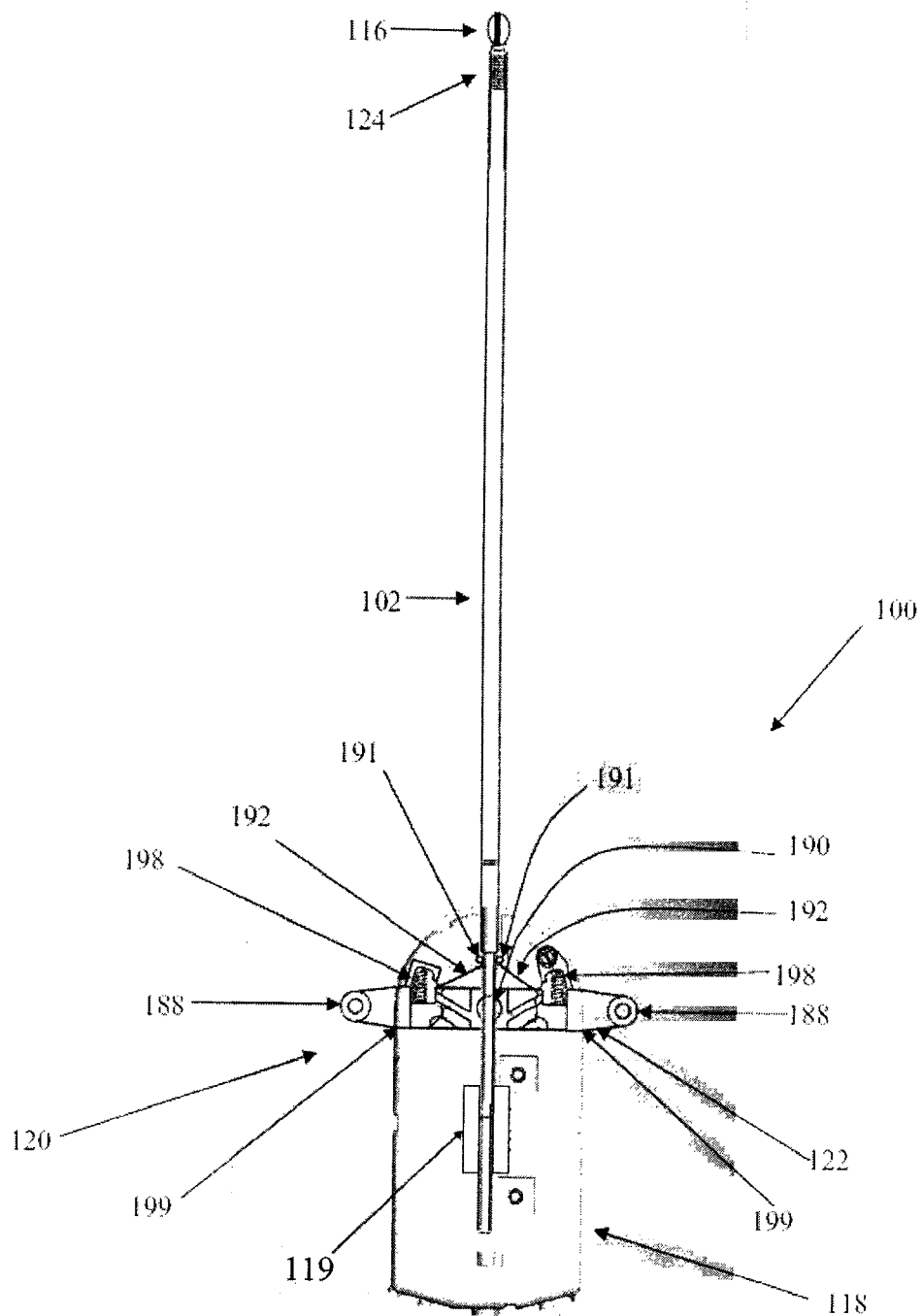
FIG. 9 is a schematic cut-away view of the housing of one embodiment of a retractor cannula device.

The steering and maneuvering of retractor assemblies and flexible regions of the tubular body may be controlled using any suitable mechanism, one example of which is shown in FIGS. 9 and 10A-10C. Referring to FIG. 9, the steering mechanism 120 is configured to cause bending of the tubular body 102 at one or more flexible regions 124. As depicted there, the steering mechanism 120 is depicted with the port tubing and a portion of the housing 118 of the retractor cannula device 100 removed. The steering mechanism comprises a lever 122 that is configured to rotate or pivot at a lever axle 190. The lever 122 is attached to two control members 192 that are slidable located along the length of the shaft 102 and are attached at a distal location of the tubular body 102. One or more posts 191 may be provided against the control members 192. In some embodiments, the posts 191 may be facilitate changes in the orientation of the control members 192, smooth sliding of the control members 192, and/or to protect other components of the retractor cannula device from cutting or other damage caused by the movement of the control members 192. In some embodiments, the ends of the control members 192 are secured to the lever 122 in one or more retaining channels or retaining structures, but in other embodiments, the control members may be proximally attached to form a control member loop that may be secured to a lever by placing the loop within a retaining channel of the lever. In some embodiments, one or more control members 192 or the control loop may be crimped, wound, sutured and/or embedded into the lever. The movement range and force may be augmented by one or more bias members 198 acting upon the lever 122. The bias members 198 may comprise helical springs as depicted in FIG. 9, but may also comprise leaf springs or any other type of bias member configuration. The movement range of the lever 122 may also be affected by the size and/or configuration of the lever openings 199 provided in the housing 118. In some embodiments, an optional locking mechanism may be provided to substantially maintain the lever in one or more positions. The control members 192 may comprise wires, threads, ribbons or other elongate structures. The flexibility and/or stiffness of the control member 192 may vary depending upon the particular steering mechanism. In further embodiments, the characteristics of the control member 192 may also vary along its length. In embodiments comprising two or more control members, the control members need not be configured symmetrically, e.g. having the same length, cross-sectional area or shape, or opposite attachment sites with respect to the longitudinal axis of the tubular shaft. Also, individual control members need not have the same configuration along their lengths.

Figure 10A:
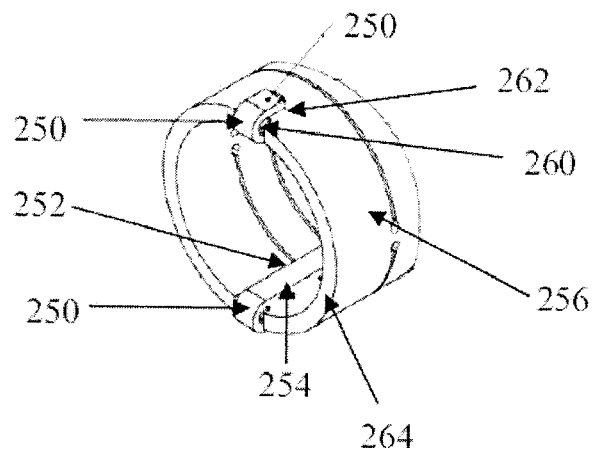
FIGS. 10A to 10C are detailed views of various embodiments of a cannula device with a steering mechanism.
Figure 10B:
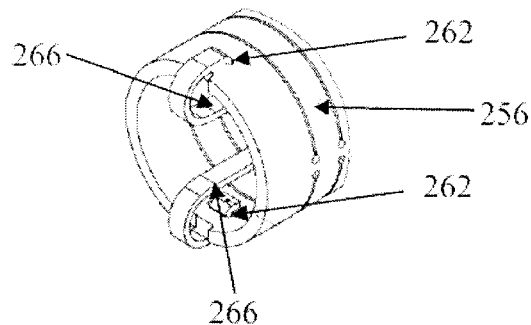
Figure 10C:
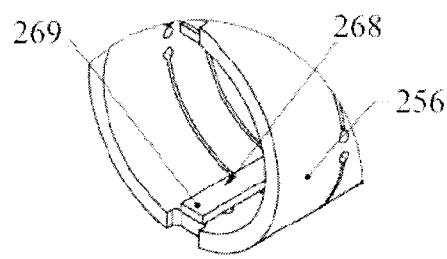

For example, although the proximal end of the control members 192 depicted in FIG. 9 comprises wire-like members, the distal ends 250 of the control members 252, illustrated in FIG. 10A, comprises ribbon structures 254. In some embodiments, the greater surface area of the ribbon structures may reduce the risk of damage to the flexible region 256 of a retractor cannula device. In the particular embodiment depicted in FIG. 10A, the ribbon structures 254 have a U-shaped configuration that forms a mechanical and/or interference fit with the flexible region 256 or other distal or flexible region of the tubular shaft. The flexible region 256 may comprise one or more notches 260, recesses or openings 262 configured to accept the ribbon structure 254. In FIG. 10A, notches 260 are provided to resist slippage of the ribbon structure 254 along the lip 264 of the flexible region 256, while the openings 262 are provided to permit insertion of the ribbon ends 264 to further augment the interfit of the ribbon structures 254 and the flexible region 256. FIG. 10B illustrates another embodiment where in the ribbon structure 266 inserts through the opening 262. In this particular embodiment, the ribbon structure 266 may also be welded or soldered back onto itself to form a loop to further secure the ribbon structure 266 to the flexible region 256. In other embodiments, as depicted in FIG. 10C, the tip 269 of the ribbon structure 268 may be bonded or soldered to the flexible region 256 or the tubular shaft, depending upon the material of the ribbon structures and the flexible region or the tubular shaft.

Figure 11A:
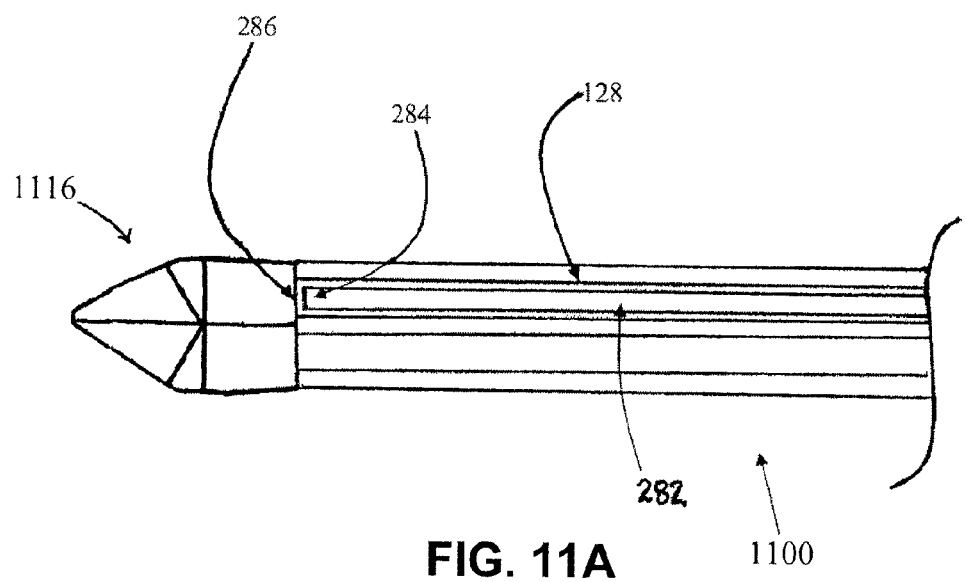
FIGS. 11A and 11B are schematic cross-sectional views of a retractor cannula device with an inserted endoscope in a neutral and a flexed position, respectively.
Figure 11B:
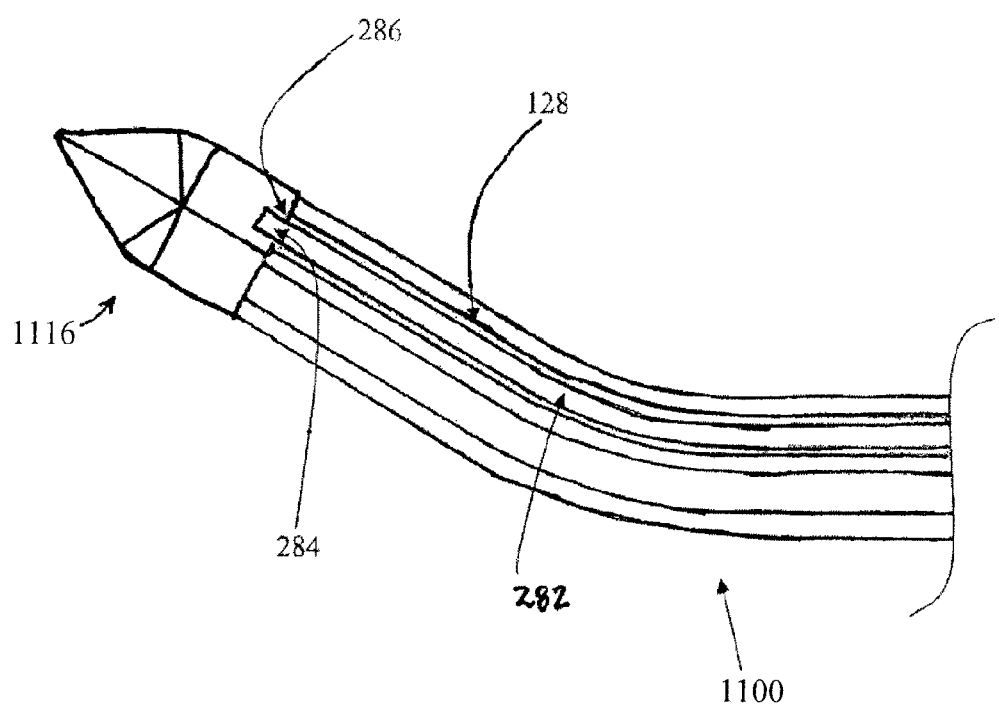

In some embodiments, during bending, one or more components inserted through the one or more channels in the tubular body of the retractor cannula device may exhibit different degrees of relative displacement. The degree of relative displacement may be affected by the degree of bending, the fixation or coupling site, if any between the component and the retractor cannula device, and/or the degree of displacement from the neutral position of the retractor cannula device. Referring to FIG. 11A, a retractor assembly 1116 of retractor cannula device 1100 shown in neutral position (e.g. straight, but may be angled or curved in other embodiments) with an endoscope 282 located in the visualization channel 128. The tip 284 of the endoscope 282 is in proximity to the end 286 of the visualization channel 128. As the retractor cannula device 1100 is flexed as shown in FIG. 11B, the tip 284 of the endoscope 282 may exhibit a relative distal displacement with respect to the end 286 of the visualization channel 128, particularly in embodiments where the endoscope 282 is coupled to the retractor cannula device 100 at a proximal location (e.g. about the housing). When the retractor cannula device 100 is flexed in the opposite direction, in some instances the endoscope 282 may exhibit a proximal retraction. To compensate for the displacement, the user may manually adjust the position of the endoscope 282 as desired.

In some embodiments, the steering mechanism may also be coupled to an endoscope adjustment mechanism so that manipulation of the steering mechanism also provides at least some position adjustment which may reduce if not eliminate the degree of displacement. In other embodiments, the endoscope may be coupled to the retractor cannula device about a distal region of the tubular body so that, during flexion, the proximal portions of the endoscope exhibit the displacement rather than the distal portions. In still other embodiments, a spring or other type of bias member may bias the endoscope distally against an interference structure (not shown) located at the distal end of the tubular body to maintain the endoscope position during flexion. In some further embodiments, the interference structure may be rotated or moved out of its interfering position to permit endoscope positioning more distally, as desired.

2. Lumens and Channels

Figure 12A:
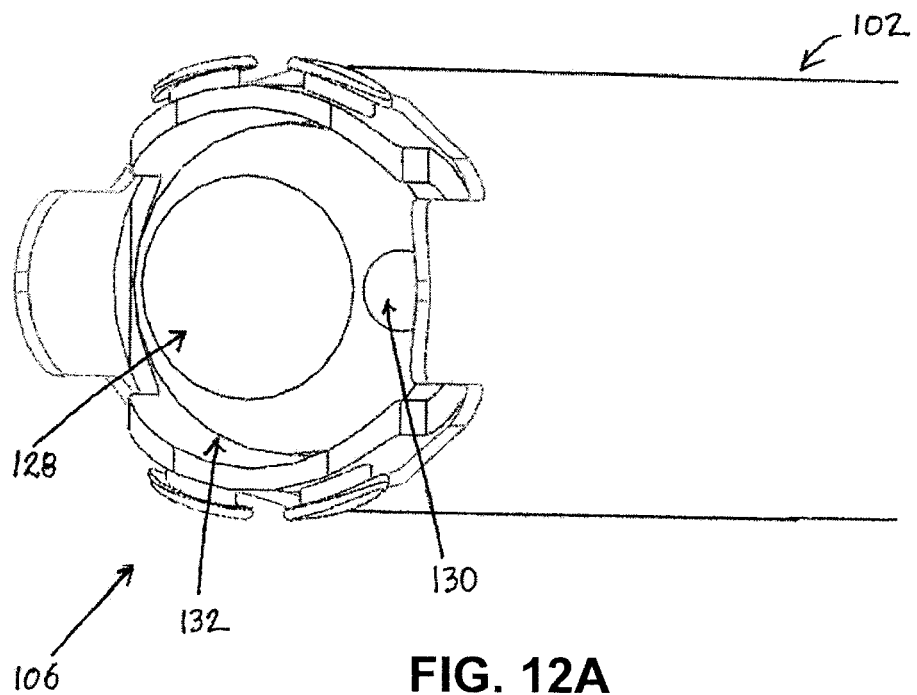
FIGS. 12A and 12B depict one embodiment of the lumens and channels within the tubular body of a retractor cannula device.
Figure 12B:
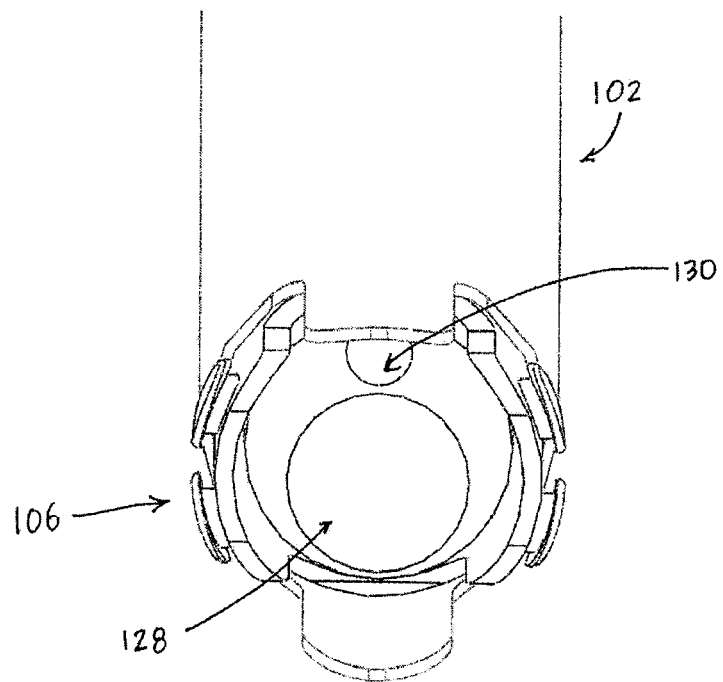

As described previously, one or more lumens or channels may be provided in the tubular body of a retractor cannula device. Lumens and/or channels may be used for the delivery of devices and therapeutic agents for a variety of functions, for example, visualization, dissection, dilation, displacement, aspiration, irrigation, infusion of medications, augmentation of tissue such as a disc, decompression of tissue such as a disc nucleus, ablation, stimulation, implantation of devices, and any other desired function. One embodiment, which is depicted in FIGS. 12A and 12B, for example, the tubular body 102 is depicted without the retractor elements to show the two channels, e.g., the visualization channel 128 and the channel 130 that open at the distal end 106 of the tubular body 102. In other embodiments, however, the tubular body may contain a different number of channels or channels with different positions, cross-sectional areas, or cross-sectional shapes, as shown in the examples in FIGS. 13A-13C and 14. Referring to FIGS. 12A and 12B, the visualization channel 128 may be used to deliver imaging devices, e.g., as an endoscopy channel, while the channel 130 may be used as a working channel for insertion of one or more instruments. Also shown is lumen 132, which may enclose at least a portion of the lumen of the tubular body 102, and may enclose at least a portion of the visualization channel 128 and the channel 130. One or more channels may have a longitudinal length that substantially spans the length of the tubular body 102, but other channels may have a length shorter than the tubular body 102, and may terminate proximal to the distal end 106. Other channels may also be used, for example, to control bending or other movements of the cannula device. One or more channels may comprise a layer or coating to facilitate sliding of instruments within the channel, including PTFE and any of a variety of biocompatible lubricious coating materials. In some embodiments, the shaft may comprise a rigid or semi-rigid material, but in other embodiments, may comprise a flexible material.

Proximally, one or more of the channels 128, 130 and 132 of the tubular body 102 may be in communication with one or more ports 108, 110, 112 and 114. In the embodiment depicted in FIG. 1, for example, the visualization channel 128 of the retractor cannula device 100 may be in communication with the port 114, which may be configured to interface with an endoscope and act as an endoscopic port. Alternatively or additionally, the channel 130 may also be in communication with the port 112, which may be configured for the insertion and delivery of instrumentation, and channel 132 may be in communication with the port 108, which may be configured to be an irrigation or aspiration port. In some embodiments, a separate irrigation port and aspiration port may be provided, which may permit simultaneous infusion and aspiration. Simultaneous infusion and aspiration may expedite clearing of the working field when compared to alternating infusion and aspiration using a single channel.

In some embodiments, the visualization channel 128 may be provided, where the visualization channel may be augmented by changes to the geometry and/or movement of the retractor assembly 116. For example, some retractor assemblies may have hinge mechanisms that allow the retractor elements or jaws to form an angle greater than about 90 degrees or greater than about 180 degrees. In other examples, retractor assemblies may have different longitudinal lengths relative to their articulation points. For example, some retractor assemblies may have a retraction element with a length of at least about 1 mm, about 2 mm, about 3 mm, about 4 mm, about 5 mm, about 6 mm or more from its articulation point with the shaft. The longitudinal lengths of each retractor element may be the same or different. The retractor cannula device used may be selected depending upon the region of the body in which the retractor cannula device has been deployed. In regions with large cavities, a rounded shape retractor assembly may be used to reduce the trauma to surrounding tissue without compromising the field of view. In regions where tissue is more densely compacted or folded, a tapered shape retractor assembly may be used because the taper of the closed configuration would allow it to maneuver into folds, and upon transitioning into the open configuration, substantially dilate the tissue to allow for a larger field of view and working space. In other examples, multiple retractor cannula devices with different configurations may be used during at the same target site.

Referring to FIGS. 12A and 12B, the visualization channel 128 may be used as a passage for insertion/removal of illumination, visualization, and/or imaging components to provide direct visualization capabilities at the distal end 106 of the retractor cannula device 100. In some embodiments, a visualization channel 128 may house or may be integrally formed with one or more illumination, visualization, analytical, and/or imaging components, including but not limited to one or more fiber-optic strands used to transmit light from a light source or to optically visualize the anatomy about the distal end 106 of tubular body 102.

The visualization channel 128 or the distal end 106 of the device 100 may include a sensor used to generate images or identify tissue or tissue characteristics. In one example, the sensor utilizes acoustic energy to generate the image, similar to diagnostic ultrasound. In another example, the sensor utilizes an electrical characteristic to generate the image or other types of structural or physiological information. In yet another example, the sensor distinguishes the type of tissue adjacent to the sensor. Some properties used by the sensor to differentiate adjacent structures or tissue include resistance, capacitance, impedance, membrane voltage, acoustic, and optical characteristic of tissue adjacent the sensor or probe. Additionally, the sensor or image may be used to distinguish different types of tissue to identify neurological tissue, collagen, or portions of the annulus, for example. It is to be appreciated that the sensor may be a multi-modal or multi-sensor probe that can distinguish bone, muscle, nerve tissue, fat, etc. to help position the probe in the proper place.

Figure 13A:
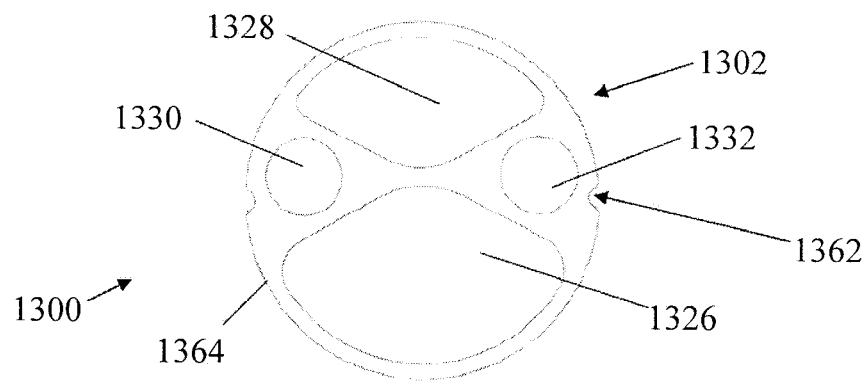
FIGS. 13A-13C are cross-sectional views of various embodiments of a multi-channel tubular body.
Figure 13B:
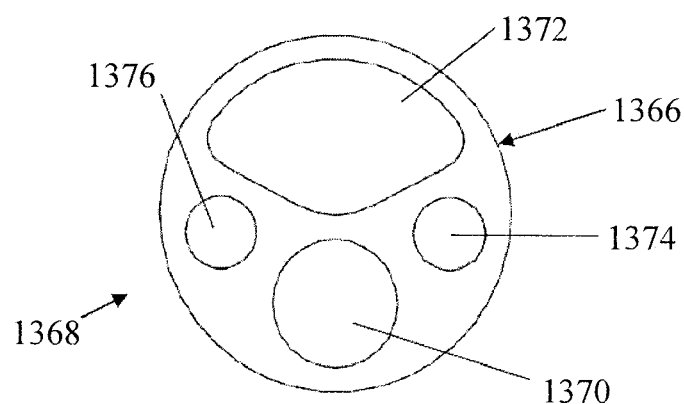
Figure 13C:
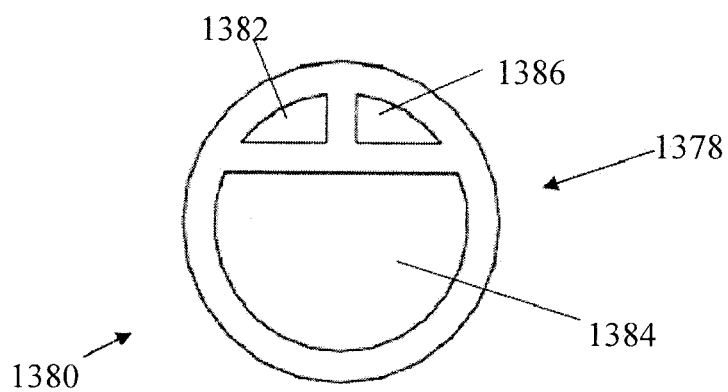

FIGS. 13A to 13C illustrate various embodiments of the retractor cannula device, where different tubular bodies may have different numbers, sizes, and shapes of lumens or channels therethrough. In FIG. 13A, the retractor cannula device 1300 may comprise a tubular body 1302 with a non-circular channel 1328 configured to house a visualization device (such as, but not limited to, an endoscope), a non-circular working channel 1326 which may be used to provide therapy device or as aspiration port, a retractor assembly actuator lumen 1332, and additional port 1330 for irrigation or aspiration. The tubular body 1302 may also optionally comprise one or more structures 1362 on its outer surface 1364. These structures 1362 may comprise recessed or protruding configurations and may be used, for example, to maintain alignment with respect to introducer or guide member, or to reduce the amount of frictional resistance from any manipulation of the retractor cannula device 1300. As depicted in FIG. 13B, the tubular body 1366 of the retractor cannula device 1368 may have a non-circular visualization or irrigation port 1370, a circular therapy device or aspiration port 1372, a circular retractor assembly actuator lumen 1374, and additional circular port 1376 for additional irrigation or additional aspiration having a greater. As demonstrated in FIG. 13B, the circular ports 1372, 1374 and 1376 need not have the same diameter. In FIG. 13C, the tubular body 1378 of the retractor cannula device 1380 has a visualization or irrigation port 1382, an injection port or therapy device or aspiration port 1384, and a retractor assembly actuator lumen 1386, wherein no port or lumen has a circular cross-sectional shape. It is contemplated that functions of various lumens in a cannula device may be suitably interchanged.

Referring back to FIG. 13A, the tubular body of the retractor cannula device 100 may include a visualization channel 1328, a larger working channel 1326, and an additional irrigation/aspiration port 1330. The channels and/or ports of the retractor cannula device 1300 may be configured to accept wide variety of therapy devices suited to the type of therapy being performed. The therapy device may be configured and used to apply energy to surrounding tissue. The therapy device may also be a surgical instrument used to cut, pierce or remove tissue. Moreover, it is to be appreciated that the therapy device may be any conventional endoscopic instrument. The therapy device may include ultrasonic devices, motor driven devices, laser-based devices, RF energy devices, thermal energy devices, cryotherapy-based devices, or other devices selected based on the spinal therapy being performed. For example, the therapy device may also be a mechanical device adapted to remove tissue such as a debrider or an aspirator. Other examples are described in greater detail below. Moreover, it is to be appreciated that the retractor cannula device 1300 may be used to inject pharmacological agents into the spinal area. The size, number and arrangement of the working channels are readily adaptable for different configurations, depending upon the type of procedures performed. A greater or a fewer number of working channels may be provided, and the working channels need not have the same size and shape. In addition, the working channels may also be configured to perform auxiliary functions. In one example the channels or ports may be used to provide irrigation to assist in tissue dissection as the atraumatic tip is advanced in the spinal space. An irrigating working channel may be in communication proximally with a fluid source, such as a syringe or intravenous infusion system, and in communication distally with the distal end of the retractor cannula device so that the fluid exiting the irrigation working channel is directed to the distal portion of the retractor cannula device. In another example, the irrigation working channel or another working channel may be used to rinse the atraumatic tip or keep clear other portions of the retractor cannula tool. In the particular embodiment depicted in FIG. 13A, the working channel 1326 and the visualization channel 1328 are configured with non-circular cross-sectional shapes. In some embodiments, the non-circular shape permits the placement of an instrument with a circular cross-sectional shape within the channel or port while providing still providing flow paths for fluids and material through the channel 126 and the visualization channel 1328. Shared or eccentric flow paths along non-circular shaft channels and ports may also otherwise take advantage of unused sections of the cannula shaft. Unlike shafts with only circular channels or ports, the flow paths may be provided without having to increase the overall cross-sectional area of the cannula shaft. Channels or ports having non-circular cross-sectional shapes may also be used with instruments having a complementary non-circular cross-sectional shape. For example, complementary non-circular cross-sectional shapes may be used to control or limit the amount of instrumentation rotation within the channel or port.

Figure 14:
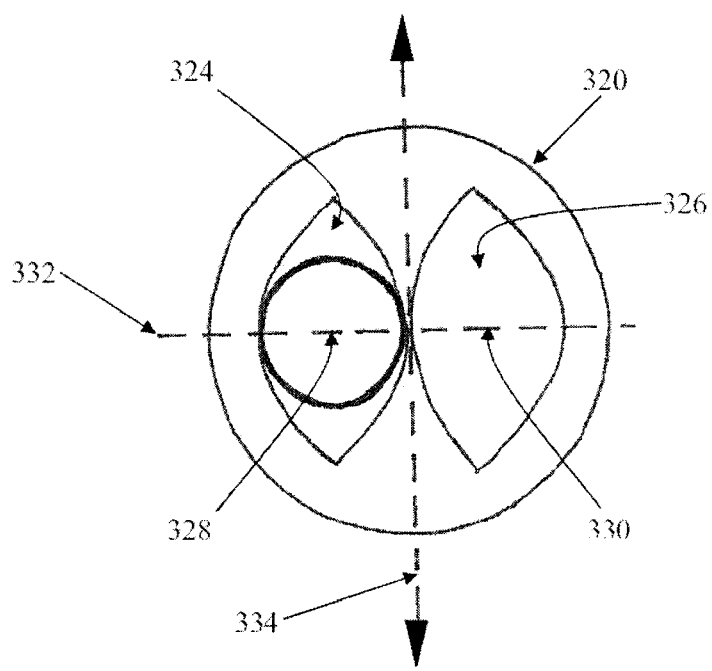
FIG. 14 is a schematic representation of one embodiment of a retractor cannula device with two channels centered along a plane perpendicular to a bending plane of the retractor cannula device.
Figure 15:
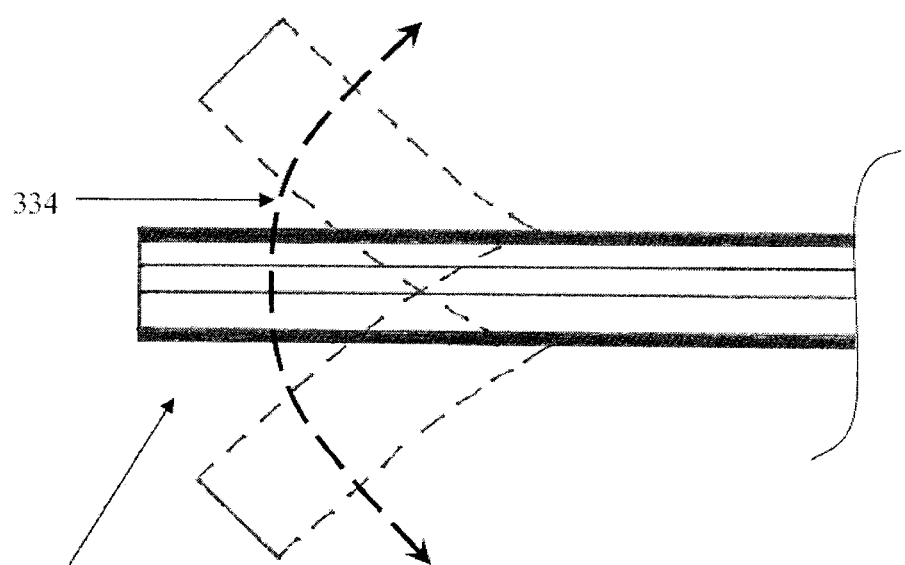
FIG. 15 is a schematic representation of one embodiment of a tubular body of a retractor cannula device in a neutral position and in various flexed positions within a bending plane (depicted with dashed lines).

FIG. 14 is a schematic representation of a tubular body 320 of one embodiment of a cannula device 322 configured for two-sided flexion within a bending plane. In some embodiments, one or more channels of the tubular shaft 320 may be configured and positioned to reduce the degree of endoscope or instrument displacement during flexion. In FIG. 15, for example, the tubular shaft 320 comprises a visualization channel 324 and a working channel 326 wherein the centers 328 and 330 of the channels 324 and 326, respectively, are located along a plane 332 that is perpendicular to a bending plane 334 of the cannula device 322. Plane 332 may be located, for example, between the midpoint of the two distal attachments of the steering mechanism. The relative position of the plane 332 and the bending plane 334 may vary depending upon the particular manner in which the steering mechanism is anchored to the flexion region. In other embodiments, the centers 328 and 330 need not be located on the plane 332, but the central location of the optics or working instruments inserted into the channels 324 and 326 are located on the plane 332. For example, a channel may be configured such that the optical center of an endoscope is substantially aligned with the plane 332, even through the weighted center of the channel and/or endoscope may not be located on the plane 332 (e.g. where the lens of the endoscope is asymmetrically located, or where the central viewing angle In embodiments comprising circular channels, the center of the channel may be the center of the circle. In other embodiments comprising non-circular channels, the center of a channel may be characterized as being coaxial with the center of the largest circular object that may be inserted into the channel.

Although the embodiment shown in FIG. 15 is directed to a cannula device having a single bending plane, in other embodiments, the cannula device may be configured with two or more bending planes. With these latter embodiments, one or more channels may be aligned with one bending plane but not another bending plane. In some embodiments, a central channel may be provided that is aligned with two or more bending planes.

In some embodiments, a trocar may be guided using fluoroscopic or other external imaging modality to place the trocar in proximity to a treatment area. In contrast to conventional procedures that attempt to fluoroscopically navigate a trocar tip around nerves and other tissue, the trocar may remain safely positioned away from sensitive structures and features. In one embodiment, the trocar tip remains about 1 to about 2 cm or more from vulnerable nerve tissue. In another embodiment, the last about 1 to about 2 cm of travel to a therapy site is performed using direct visualization provided by a visualization mechanism in the retractor cannula device.

In some embodiments, the trocar is removed and the retractor cannula device 100 is inserted into the pathway formed by the trocar. In other embodiments, a tubular trocar may be used. From the final trocar position, the retractor cannula device 100 may be passed through a channel or lumen of the trocar and along the remaining distance to the therapy or treatment site using the onboard visualization capabilities. The onboard visualization may be used alone or in combination with the retractor assembly 116 or other type of atraumatic tip to identify, atraumatically displace, and/or maneuver around nerves and other tissue as needed. An optional steering mechanism may be provided on the retractor cannula device 100 to manipulate surrounding tissue and structures, and/or to traverse the remaining distance to one or more therapy or treatment sites. In other embodiments, the retractor cannula device 100 may have a rigid or fixed configuration, and may be manipulated by optionally manipulating the trocar to reach a desired location. In an alternative embodiment, the trocar may house the retractor cannula device during trocar insertion and thus utilize the direct visualization capabilities of the visualization mechanism within the retractor cannula device to guide trocar positioning. In still another embodiment, the trocar may be provided with a separate imaging system from the imaging device or component provided in the retractor cannula device for use during trocar insertion. In still another embodiment, the trocar may be configured with a lumen to house only the imaging component from the retractor cannula device 100. After the desired trocar position is reached, the trocar is removed and the imaging component is removed from the trocar and reinserted into the retractor cannula device 100. In yet another alternative embodiment, both external imaging may be used to position the trocar distal end, either alone or in combination with direct imaging.

2. Handle Portion

Figure 16:
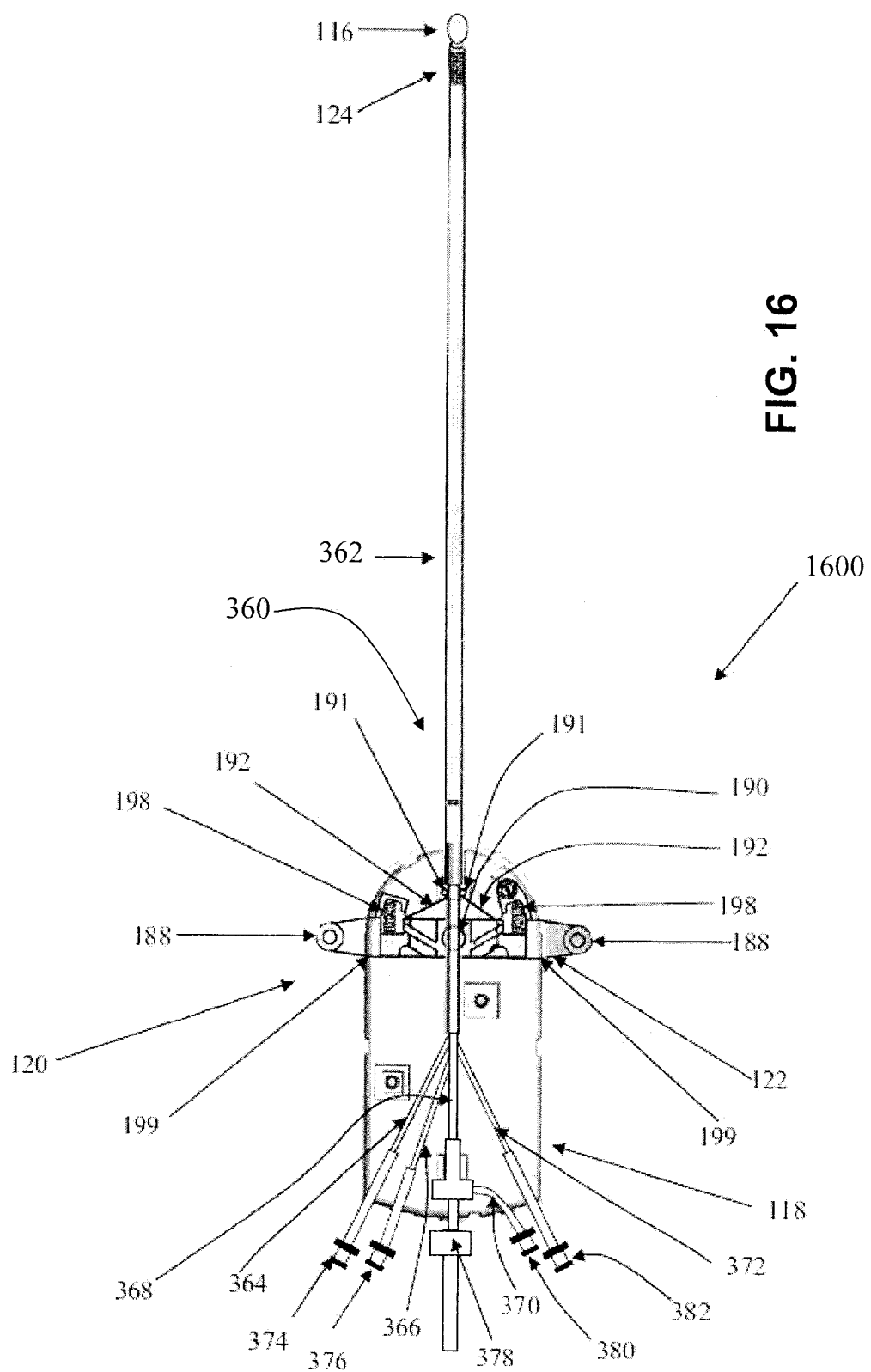
FIG. 16 is a cut-away view of a retractor cannula device with tubes connected to the tubular body.
Figure 17:
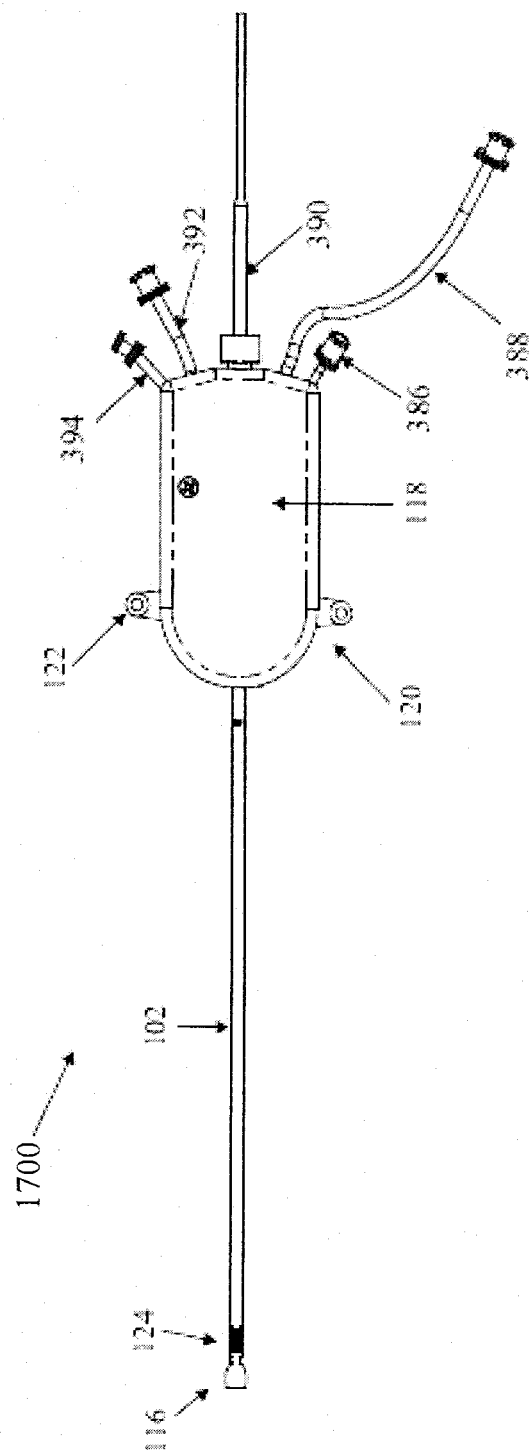
FIG. 17 is a side elevational view of a retractor cannula device.

As described previously, a retractor cannula device may be provided with a handle, e.g., handle 118, to control the navigation and use of the tubular body and retractor assembly. The handle may also serve as an interface between a variety of functional ports and the longitudinal channels and/or lumens of the tubular body, where the channels and lumens of the tubular body may be continuous with lumens and channels of the retractor assembly. Referring now to FIG. 16, the proximal end 360 of the tubular body 362 may be coupled to one or more tubing segments 364, 366, 368, 370, 372 that correspond to one or more channels and connectors 374, 376, 378, 380, and 382 of the retractor cannula device 1600, respectively. As noted in FIG. 16, a tubing segment 370 may be in communication with another tubing segment, such as the tubing segment 368, which connected to the working channel of the device 382. This particular tubing segment 370 may be used, for example, to flush or aspirate fluid or material inserted into the working channel of the device 382 that is accessed through the middle port 378 and tubing segment 368. The particular design features of a tubing segment may vary, depending upon the particular function. The connector coupled to a particular tubing segment may comprise any of a variety of connectors or instrument interfaces. In some embodiments, for example, one or more connectors may comprise a standardized connector such as Luer lock, while in other embodiments, the connector may be a proprietary connectors. Depending upon the particular channel, in some embodiments, a check valve, septum, or a hemostasis valve may be provided to resist retrograde flow of fluid out of the device. The characteristics of a particular channel, including its dimensions and flexibility or rigidity, may depend upon its particular use. In FIG. 17, for example, a retractor cannula device 1700 comprises five ports 386, 388, 390, 392 and 394, wherein the longer, flexible ports 388 and 392 may be used for infusion or aspiration. Such ports may be beneficial to facilitate the attachment of a bulky item such as a syringe. A rigid port, such as port 390, may be provided for instruments that may otherwise be damaged or are difficult to pass through tubing that may exhibit greater frictional resistance.

The therapy device may be supplied with energy from a source external using a suitable transmission mode. For example, laser energy may be generated external to the body and then transmitted by optical fibers for delivery via an appropriate therapy device. Alternately, the therapy device may generate or convert energy at the therapy site, for example electric current from an external source carried to a resistive heating element within the therapy device. If energy is supplied to the therapy device, transmission of energy may be through any energy transmission means, such as wire, lumen, thermal conductor, or fiber-optic strand. Additionally, the therapy device may deliver electromagnetic energy, including but not limited to radio waves, microwaves, infrared light, visible light, and ultraviolet light. The electromagnetic energy may be in incoherent or laser form. The energy in laser form may be collimated or defocused. The energy delivered to a disc may also be electric current, ultrasound waves, or thermal energy from a heating element. Moreover, it is to be appreciated that embodiments of the retractor cannula devices described herein may also be used to dispense a compound, compounds or other pharmacological agents to reduce, diminish or minimize epidural neural tissue scarring.

As noted in the embodiment depicted in FIG. 1, the visualization channel 128 provides access to the target area for endoscopic imaging and/or medical imaging components. The retractor elements of a retractor assembly in the open configuration may act as dilators or retractors to permit a wider field of view. For example, the retractor cannula device may first assume a closed configuration in order to atraumatically navigate towards the target body region. Once the distal end of the shaft has reached the target area, a retractor assembly can be transitioned to the open configuration, dilating the surrounding tissue and enabling an endoscope positioned in visualization channel 128 to visually access the target tissue. In some embodiments, the retractor elements of the retractor assembly may be made of a transparent material, so that even in the closed configuration, the endoscope residing in visualization channel 128 may have visual access to the surrounding tissue, and may allow the endoscope to be used to provide visual cues to navigate the distal tip of the cannula to the desired location.

As mentioned previously, an endoscope or working instrument (e.g. grasper(s), balloon(s) or tissue debrider) may be inserted into one or more channels of the cannula device through a proximal port. The proximal port, endoscope, and/or working instrument may be optionally configured with one or more features to lock and/or adjust the position of the inserted component. In other embodiments, one or more components of the endoscope or working instrument may be an integrally formed component of the cannula device and is not configured for removal.

Figure 18A:
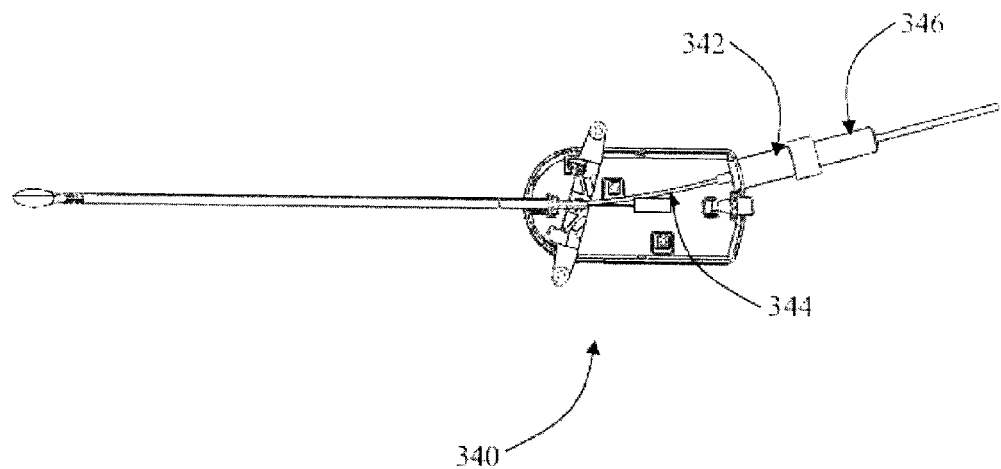
FIG. 18A is a cut-away view and FIG. 18B is a side elevational view of one embodiment of a retractor cannula device with an endoscopic coupling port.
Figure 18B:
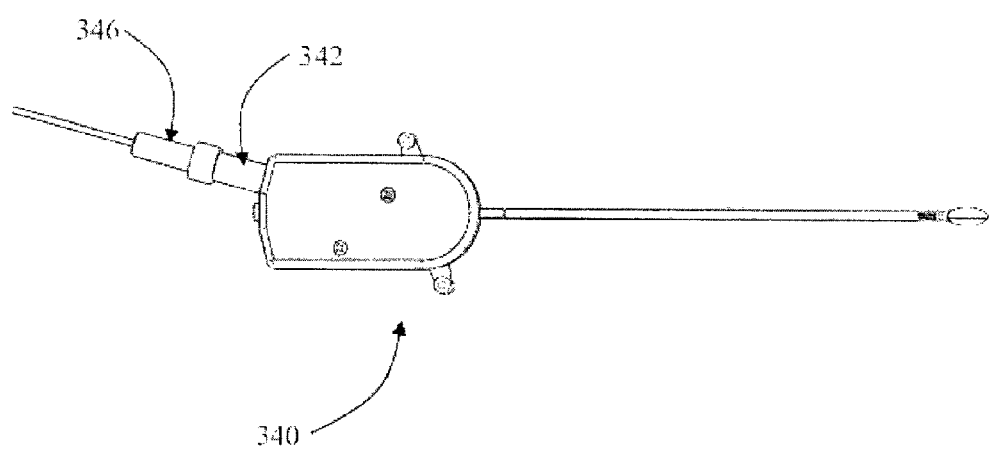

For example, in FIGS. 18A and 18B, a retractor cannula device 340 is configured with a scope port 342 in communication with the visualization channel (not shown) with a segment of tubing 344. The scope port 342 may comprise a lumen with a viscoelastic or friction surface material that is configured to slidably grip an inserted endoscope. The slidably grippable materials may include but are not limited to silicone, a urethane, including viscoelastic urethanes such as SORBOTHANE® (Kent, Ohio) and any of a variety of styrenic block copolymers such as some made by KRATON® Polymers (Houston, Tex.). The scope port 342 thus need not have any particular clamp or locking mechanism to secure the endoscope or working instrument to the scope port 243, nor any particular adjustment mechanism. In other embodiments, however, the scope port may comprise a releasable lock or clamp mechanism designed to couple to the endoscope or working instrument, with an optional adjustment assembly that may be used to modify the spacing between the lock or clamp mechanism and the housing.

Figure 23A:
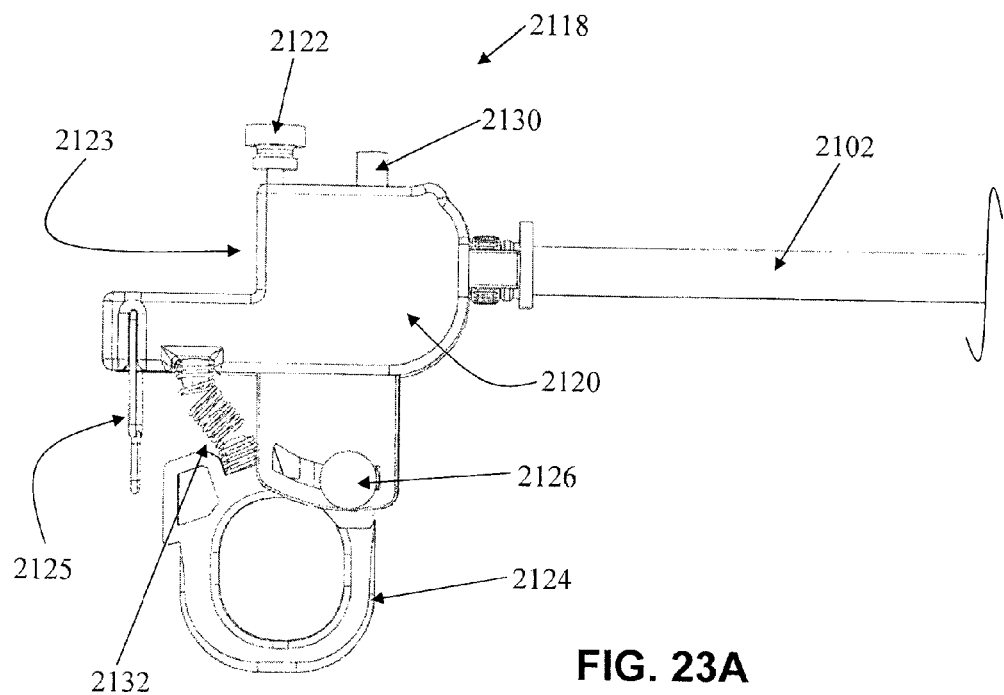
FIG. 23A is a side view of one variation of a handle of the retractor cannula device from FIGS. 21A and 21B.
Figure 23B:
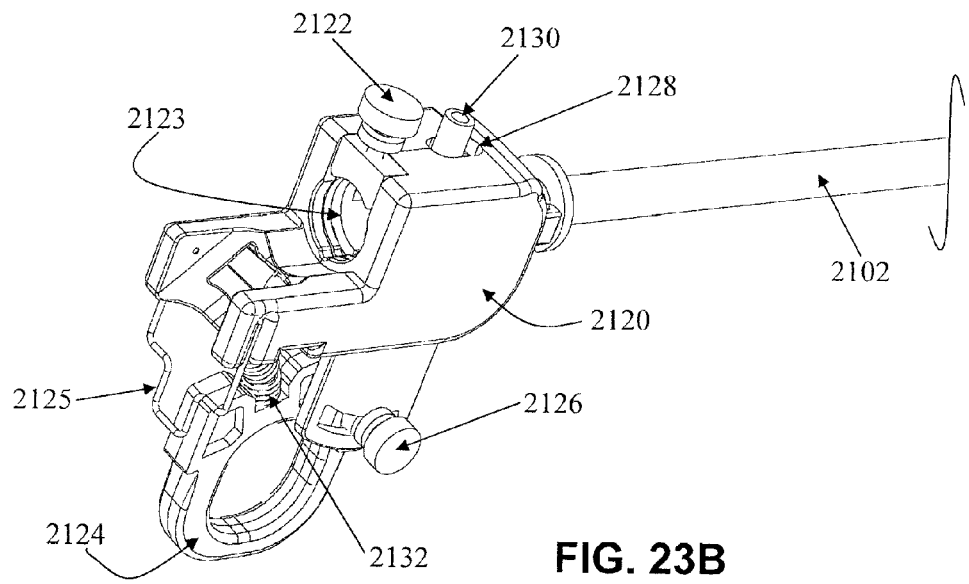
FIG. 23B is a perspective view of the handle from FIG. 23A.

Another variation of a handle that may be used with the devices and methods described above is shown in FIGS. 23A and 23B. FIG. 23A is a side-view of the handle 2118, which may comprise a housing 2120 which is shaped and sized to accommodate various ports and actuators as previously described. For example, the housing 2120 may have apertures to accommodate the handle port 2123, and optionally, the auxiliary port 2130. The auxiliary port 2130 as shown in FIGS. 23A and 23B retains a tube 2130, but in other variations, may retain a plug or valve. For example, where the auxiliary port 2130 is used as a saline flush port, the tube 2130 may be sized to fit with other valves or tubes connected to a saline reservoir. When not in use, the auxiliary port 2128 may be occluded with a plug, which may help to prevent accidental insertion of fluids or devices. The handle port 2123, depicted in FIG. 23B, may be configured to accommodate any of the previously described devices, for example, a visualization device (e.g., an endoscope), or other tissue-manipulating devices (e.g., for extracting or dissecting tissue). One or both the handle port 2123 and the auxiliary port 2128 may be in communication with one or more lumens in the tubular body 2102. Devices may be coupled to the handle 2118 by the device coupler 2122, which may be a pin, screw, clip, etc. that is configured to secure a device to the handle 2118. The device coupler 2122 may also secure a device by friction-fit, form-fit, snap-fit, bonding by adhesives or Velcro™, and the like.

The handle 2118 may also have any number and type of actuators for controlling the navigation of the tubular body 2102, as well as for controlling the configuration of the retractor assembly attached at the distal end of the tubular body. For example, the pivot lever 2124 may be used to transition the retractor assembly associated with handle 2118 (e.g., any of the retractor assemblies described previously may be used here) from a closed to an open configuration. A resistance pin 2126 may be included to regulate the actuation force of the pivot lever 2124. Optionally, the bias spring 2132 may be coupled with the pivot lever 2124 to bias it into one configuration, for example, the closed configuration. The length, spring constant, and other features of the bias spring 2132 may be selected to bias the pivot lever 2124 (and in turn, bias the retractor assembly) into any configuration as desired. The pivot lever lock 2125 may also be included to restrict the actuation of the pivot lever 2124. As with the handles described previously, any number of ports, tubes, and actuators may be included according to the different devices that may be used during various procedures on a body.

C. Methods

A retractor cannula device may be used for a variety of functions, which may be performed in a variety of procedures on a body. A retractor cannula device may be used for visualization, dissection, dilation, displacement, aspiration, irrigation, infusion of medications, augmentation of tissue such as a disc, decompression of tissue such as a disc nucleus, ablation, stimulation, implantation of devices, and any other desired function. Such a device may be used in medical procedures such as tissue biopsy, disc augmentation, nucleus decompression, nucleus abrasion, as well as for the repair of a herniated disc, and for the diagnosis of disc degeneration. Other procedures, such as the implantation of devices to structurally support a disc annulus, or to shrink a portion of the nucleus or annulus, or sealing an annulus, may use one or more of the devices and components described above.

During use, the retractor cannula device may be moved or may remain in place while an inserted therapy device is manipulated to perform the desired function. Once the working or therapy area has been created or accessed using the atraumatic retractor assembly, the atraumatic retractor assembly may be removed thereby allowing working channel or trocar or introducer to be used for another instrument or therapy device or to provide support for a procedure. For example, the therapy device may comprise a mechanical debrider or other type of tissue disrupting device that may be introduced via the working channel to assist in removal of tissue. Various examples of mechanical tissue disrupting devices that may be used with a retractor cannula device are described in U.S. patent Ser. No. 12/035,323, filed Feb. 21, 2008, which was previously by incorporated by reference in its entirety. In yet another example of the flexibility of the retractor cannula device, one or more the working channels or ports may be used to provide access for the delivery of pharmacological agents to the access site either for application onto or injection into tissue. In some embodiments, the therapeutic agents may be directed injected into the channel or port, but in other embodiments, an infusion catheter may be inserted into a channel or port and used to provide additional control of the therapy. The infusion catheter may have any of a variety of configurations and features, including but not limited to its own optional steering mechanism separate from the retractor cannula device, and a needle tip for injecting therapeutic agents into the tissues or structures. In some embodiments, the needle tip may be retractable and extendable to protect against inadvertent puncture of the tissues or structures accessible from the retractor cannula device. Examples of injection catheters that may be used with embodiments of the retractor cannula device include U.S. patent Ser. No. 10/820,183, which is hereby incorporated by reference in its entirety.

Figure 19:
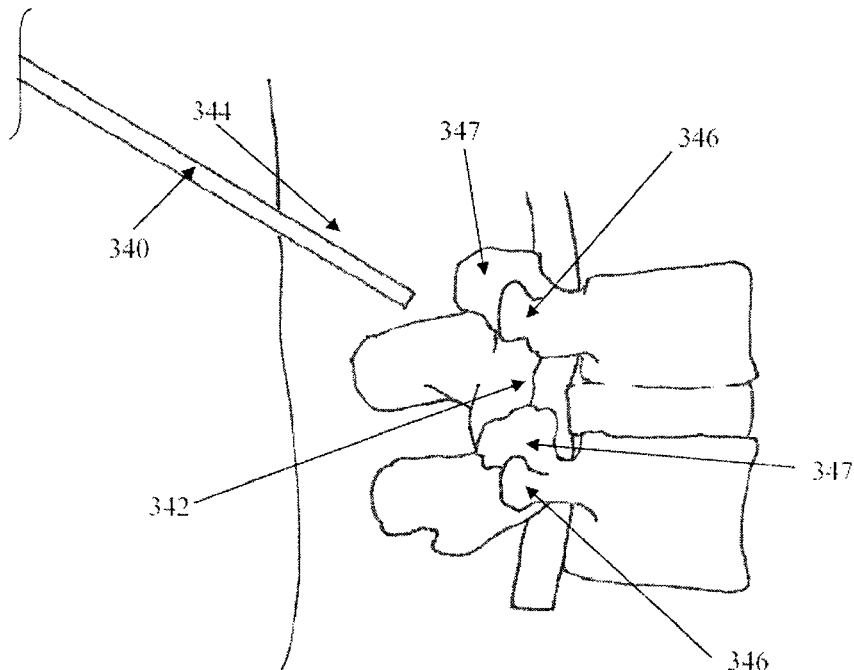
FIG. 19 is a schematic side cut-away view of one approach to the vertebrae.
Figure 20:
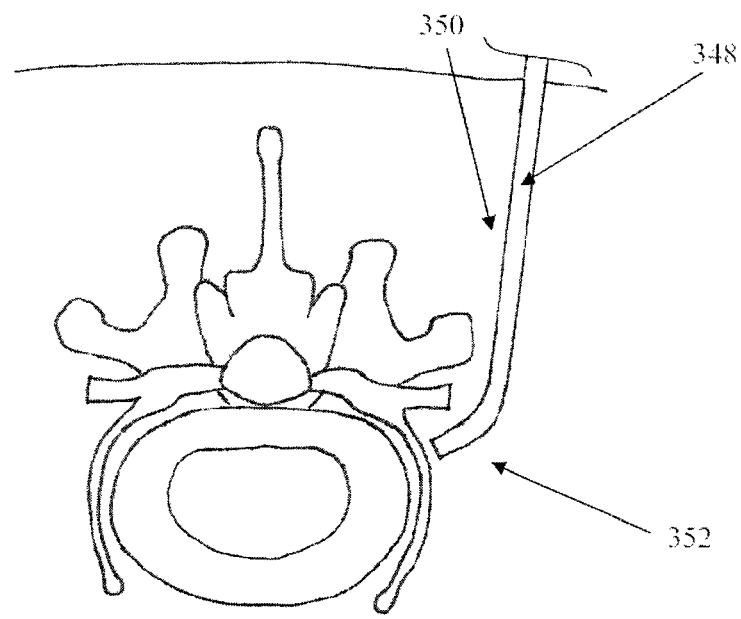
FIG. 20 is a schematic superior cut-away view of one approach to the vertebrae.

The flexion of the retractor cannula device may facilitate access to the target site and/or reduce the degree of tissue disruption in achieving access to the target site. For example, in some procedures, the angle for approaching the target site through the skin may be different from the angle that provides the visibility or viewing angle to treat or diagnose a particular abnormality. Referring to FIG. 19, in some embodiments, a cannula system 340 may be inserted to a target site 342 by utilizing longer or indirect access pathways 344 in order to achieve the desired approach angle to a target site, and/or to avoid interference from structures such as the transverse spinal processes 346. By using a steerable cannula system 348 as depicted in FIG. 20, however, a shorter or a more direct insertion pathway 350 may be taken to a target site 352, which may reduce the aggregate degree of tissue disruption compared to a longer insertion pathway. By taking advantage of the steerability of the cannula system 348, the desired approach angle to a target site may be achieved.

The retractor cannula device may also be used to perform denervation procedures using direct visualization from the retractor cannula device. The denervation procedure may be physical, chemical or electrical denervation, for example. The approaches used may be similar those described herein to access the posterior or posterolateral annulus. It is to be appreciated that the denervation procedures may be performed to relieve discogenic pain and/or before the disc damage has progressed to a herniated disc or torn annulus.

The retractor cannula devices may be used, for example, in systems for treating disc degeneration that include nucleus decompression devices. The retractor cannula device may be used for accessing the nucleus and delivering a nucleus decompression device. For example, a decompression device may be advanced from one of the working channels of the retractor cannula device and into the nucleus of a disc. A nucleus decompression device may be used to removed the disc nucleus tissue either by dissection, suction, dissolving, or by shrinking the nucleus. Various types of thermal energy are known to shrink the nucleus such as resistive heat, radiofrequency, coherent and incoherent light, microwave, ultrasound or liquid thermal jet energies. Mechanical tissue removal devices may also be used. Decompression of the disc nucleus may result in the protruded disc material collapsing toward the center of the disc. This may reduce the pressure on the spine nerve roots, thereby minimizing or reducing the associated pain, weakness and/or numbness in the lower extremities, upper extremities, or neck region. One or more devices that may be used to strengthen and/or support the weakened disc wall may also be used with a retractor cannula device.

In addition to spinal applications, the atraumatic cannula system may also be used for a variety of other procedures. The atraumatic cannula system, including the retractor cannula systems, may be used to provide direct visualization to a variety of both bedside and surgical procedures that were previously performed blind and/or with indirect visualization. Such procedures include but are not limited to pleural biopsy, pleuracentesis, paracentesis, renal biopsy, and joint aspiration, for example. In another example, the cannula system may be used in the emergency room or trauma centers to perform peritoneal taps to diagnosis blunt abdominal trauma.

In some embodiments, the retractor cannula device may be used for diagnostic purposes. Because of the complexity of the spine, it may be more difficult to diagnose an injury than for other medical conditions. As such, the direct visualization capabilities of the subject devices may be able to accurately identify any instability or deformity in the spine. For example, the subject device may offer direct visualization of any tumors, fractures, nerve damage, or disc degeneration. In addition, the subject devices may include sensors for collecting diagnostic data, for example, sensors that measure flow, temperature, pressure, or oxygen concentration. The subject devices may also be used to remove fluid, tissue or bone samples to be used for external diagnostic tests. Additionally, the subject devices may deliver testing reagents or additional instruments for diagnosing disc degeneration and bony degeneration, for example, the subject devices may deliver electrodes for diagnosis and treatment.

In one embodiment, the retractor cannula device may be used to perform discectomy. In this particular embodiment, the patient is prepped and draped in usual sterile fashion and in a lateral decubitis or prone position. General, regional, or local anesthesia is achieved and a rigid guidewire may be inserted percutaneously to the epidural space. Guidewire placement may be performed under fluoroscopic guidance or other types of indirect visualization including ultrasound. In some instances, a small skin puncture or incision is made about 2 to 5 inches from the midline of the patient's lumbar region to facilitate guidewire insertion. A needle may also be used to facilitate guidewire passage through some tissues. The guidewire may introduced on the ipsilateral side from which the nerve impingement has been identified and at an angle of about 25 degrees to about 45 degrees to the patient's back, but in other procedures, a contralateral approach and/or a different angle may be used. After confirmation of the guidewire location, a dilator may or may not be inserted over the guidewire to enlarge the guidewire path to the epidural space. An introducer with a releasable lock may be inserted over the dilator to maintain access so that the dilator and guidewire may be removed. An endoscope or other type of direct visualization may be inserted into the scope channel of the retractor cannula device. An irrigation fluid source is connected to the irrigation port on the retractor cannula and activated to provide continuous flushing. A passive or active aspiration port or outlet port is checked for patency. The retractor cannula is inserted into the introducer and advanced toward the epidural space. Direct visualization of the epidural space may be performed with the endoscope as the retractor cannula nears the epidural space. As the retractor cannula enters the epidural space, the retractor assembly may be manipulated (e.g. flexed and/or rotated) to orient the user and to identify the spinal nerve and for any disc or foraminal pathology. The retractor cannula device may then be advanced closer to the treatment site. Where the treatment site is abutting or impinging upon a nerve, the retractor assembly in the open configuration may be used to separate the treatment site and the nerve and to create a working space at the treatment site. In some embodiments, a guidewire may be reinserted into a channel of the retractor cannula and advanced past the tip of the retractor assembly toward the treatment site. For example, the guidewire may be inserted into a bulging region of the annular wall at the site of impingement. Insertion may occur before or after the retractor assembly is urged into the open configuration, and before or after a nerve is separated from a bulging disc surface. Under visual guidance, the open jaws of the retractor assembly may be directed towards the tissue to be removed, and then urged to the closed configuration, thus grasping the tissue. Appropriate maneuvering techniques may then be applied to remove the tissue gripped by the jaws of the retractor assembly. Alternatively or additionally, a tissue disrupting instrument may be inserted in the retractor cannula device and activated to mince or disrupt the tissue at the treatment site. For example, the retractor cannula device may be configured to house an automated auger, which can be turned on to spin within the chamber space enclosed by the retractor assembly to quickly remove tissue. Alternatively or additionally, negative pressure may be applied through the auger to draw the tissue targeted for removal into the working channel. The disrupted material may be swept away by the continuous irrigation and flush system, or may be removed from the treatment site by an aspiration assembly on the tissue disrupting instrument, or secured by the jaws of the retractor assembly which is then withdrawn distally. A coagulation probe, if needed, may be inserted into the retractor cannula to achieve hemostasis and/or to shrink tissue. In some embodiments, the treated disc surface may self-seal due to the small size of the tissue disrupting instrument and/or the reduced pressure in that portion of the disc following removal of disc material. In other embodiments, the treated disc may be further treated to reduce any extrusion of disc material from the treatment site. A forceps or additional grasper instruments may also be used with the retractor cannula device to remove any extra-discal fragments. In some instances where fragments may have migrated through a foramen of the vertebrae, the size of the retractor cannula may permit advancement of the retractor cannula into or even through the foramen. Thus, the retractor cannula device may be inserted into the central spinal canal from the foramen to retrieve any migrated fragments.

In another embodiment, a retractor cannula system may be utilized for any of a variety of cardiothoracic procedures, including but not limited to bronchoscopy, pleural biopsy, pleuracentesis pericardiocentesis, and pericardial biopsy. Pericardial biopsy, for example, is indicated for the investigation of a pericardial effusion. The procedure may be performed under fluoroscopic guidance or using endoscopic instruments, but is still associated with substantial morbidity, including but not limited to risks of a pneumothorax and myocardial rupture. A minimally invasive, direct visualization alternative may improve the risk/benefit profile of the procedure. In one particular embodiment, the patient is prepped and draped in usual sterile fashion. Local anesthesia is achieved in the subxiphoid region of the patient. In other embodiments, other entry points into the thoracic cavity may be used instead. In other embodiments, regional or general anesthesia may be used instead. In some embodiments where a pericardial drainage catheter was already in place, the guidewire may be inserted into the catheter and the catheter may be removed, leaving the guidewire in place. The guidewire may be a straight guidewire or a J-tip guidewire, for example. In embodiments where an initial entry into the pericardial space is made by the guidewire, a catheter may be inserted over the guidewire and one or more pericardial fluid samples may be taken for chemistry, histology, and/or culture, for example, before continuing the procedure. One or more dilators may be inserted over the guidewire and removed to widen the tissue pathway from the skin to the pericardial space. After widening the guidewire pathway, the retractor cannula system may be inserted over the guidewire. In some embodiments, as the retractor cannula system is inserted, a sampling of the parietal pericardial tissue (i.e. the outer pericardial surface) may be taken before or after the placement of the retractor cannula system into the pericardial space. In some embodiments, the retractor assembly may be in the open configuration and pressed against the parietal pericardial surface. An additional retractor assembly may be used to take one or more tissue biopsies of the parietal pericardial surface. A coagulation probe may be used to provide hemostasis following the biopsy or biopsies. The retractor cannula may be placed in the closed configuration and advanced distally over the guidewire toward the pericardial space. Once in the pericardial space, the guidewire is optionally removed from the retractor cannula system. The pericardial fluid may be drained and replaced with saline or a gas to facilitate viewing. In patients with a hemorrhagic effusion, additional irrigation and/or drainage may be used to improve the clarity of the viewing field. The retractor assembly may be placed in the open configuration and the pericardial space may be explored by flexing and/or rotating the retractor cannula device. In some embodiments, the retractor cannula may be flexed in a retrograde fashion and the extended retractor assembly tip of the retractor cannula is used to atraumatically tent up the pericardial tissue to reduce the tissue laxity and increase the success of the biopsy. Unlike traditional endoscopic procedures, which are sometimes contraindicated when there is insufficient fluid or loculated fluid in the pericardial sac, use of the tapered shape retractor cannula system may facilitate tissue separation between the pericardium and the epicardium to safely perform the biopsy in those situations. Tissue biopsies of the visceral pericardium and/or the epicardium may be taken using graspers or other endoscopic biopsy tools. Using a tissue debrider and/or a coagulation probe, one or more windows or fenestrations may be formed in the pericardium to provide ongoing drainage of the pericardial effusion. Pericardial windows or fenestrations, if any, may be performed before or after entry into the pericardial space. The retractor cannula may then be removed and an x-ray may be taken to check for a pneumothorax. If needed, chest tube drainage may be provided until the pneumothorax has resolved.

In another embodiment, the retractor cannula system may be used to perform any of a variety of genitourinary and OB/GYN procedures, including but not limited to cystoscopy (with or without bladder biopsy), renal biopsy, prostate biopsy and surgery, fetoscopy (including optional fetal blood draws), and bladder neck suspension procedures. In one particular example, cystoscopy may be performed using a flexible retractor cannula system with a forward-positioned extendable retractor assembly, but in other embodiments, a rigid retractor cannula system may also be used. In one embodiment, a cystoscopy procedure may be performed by draping a patient in the usual fashion and prepping the urethral orifice with a sterilizing agent and a topical anesthetic. In patients where ureteroscopy may be performed in addition to cystoscopy, regional or general anesthesia may be used instead. A topical anesthetic is optionally applied to the exterior of the retractor cannula system as the retractor cannula system is inserted into the urethral orifice and advanced to the bladder cavity. In some embodiments, the bladder may be filled with a gas or a liquid to expand the bladder wall for viewing. Once in the bladder, the retractor cannula system may be flexed and rotated to view the bladder cavity. Biopsies may be taken as indicated by inserting a biopsy instrument (e.g. a grasper) into a channel of the retractor cannula device, actuating the biopsy instrument and withdrawing the biopsy instrument. The ureteral orifice may be identified and the retractor cannula may be inserted into the ureter. A guidewire may be optionally inserted through the retractor cannula system and into the ureteral orifice to facilitate passage of the retractor cannula system into the ureter. In some embodiments, the retractor assembly of the retractor cannula system may be at least partially expanded during entry and/or advancement of the device, to reduce the risk of ureteral perforation. Depending upon the length of the retractor cannula system, the retractor cannula system may also be advanced into the intrarenal collecting system. If a stone is encountered during the procedure, the jaws of the retractor assembly may be actuated to remove the stone. Alternatively or additionally, a basket or other type of capturing instrument may also be inserted into the retractor cannula system to remove the stone. For stones that are too large to be withdrawn through a channel of the retractor cannula system, a burr or other type of disrupting structure may be used to break up the stone. Once the biopsies and/or stone break-up or removal is completed, the retractor cannula system may be withdrawn.

It is to be understood that this invention is not limited to particular exemplary embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, some potential and preferred methods and materials are now described. All publications mentioned herein are incorporated herein by reference to disclose and describe the methods and/or materials in connection with which the publications are cited. It is understood that the present disclosure supersedes any disclosure of an incorporated publication to the extent there is a contradiction.

It must be noted that as used herein and in the appended claims, the singular forms "a", "an", and "the" include plural referents unless the context clearly dictates otherwise. Thus, for example, reference to "a blade" includes a plurality of such blades and reference to "the energy source" includes reference to one or more sources of energy and equivalents thereof known to those skilled in the art, and so forth.

The publications discussed herein are provided solely for their disclosure. Nothing herein is to be construed as an admission that the present invention is not entitled to antedate such publication by virtue of prior invention. Further, the dates of publication provided, if any, may be different from the actual publication dates which may need to be independently confirmed.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims. For all the embodiments described herein, the steps of the method need not be performed sequentially.

The invention claimed is:

1. A retractor cannula device comprising:
a first tubular body having a central axis and a distal end, the tubular body comprising at least one lumen configured to hold an endoscope;
a second tubular body slidably positioned within the first tubular body; and
a retractor assembly located at the distal end of the tubular body, the retractor assembly including at least one movable element having a distal tip, and having a first closed configuration and a second open configuration, the retractor assembly coupled to the first tubular body through a living hinge, the retractor assembly further coupled to the second tubular body, such that, the retractor assembly transitions from the first closed configuration to the second open configuration in response to movement of the second tubular member in a direction toward the retractor assembly, the distal tip of a first of the at least one moveable element configured to pass through the central axis of the tubular body as the retractor assembly transitions from the first closed configuration to the second open configuration.

2. The device of claim 1, further comprising an endoscopic system.

3. The device of claim 1, wherein the at least one movable element comprising a curved surface.

4. The device of claim 3, wherein the curved surface of each movable element is uniformly oriented around a longitudinal axis of the retractor cannula device to generally form a rounded tip in the first closed configuration.

5. The device of claim 4, wherein the retractor assembly comprises at least two movable elements.

6. The device of claim 3, wherein the curved surface of each of the at least one movable element is non-uniformly oriented around a longitudinal axis of the retractor cannula device to form a tapered tip in the first closed configuration.

7. The device of claim 6, wherein the tapered tip comprises a linear taper region.

8. The device of claim 3, wherein the curved surface of at least one movable element is non-uniformly and asymmetrically oriented around a longitudinal axis of the retractor cannula device to form an angled tip.

9. The device of claim 8, wherein the angled tip is oriented across a longitudinal midline of the retractor assembly.

10. The device of claim 3, wherein a cross-section of the retractor assembly perpendicular to a longitudinal axis of the device comprises a non-circular configuration.

11. The device of claim 3, wherein a cross-section of the retractor assembly perpendicular to a longitudinal axis of the device comprises at least one linear region.

12. The device of claim 3, wherein the curved surface comprises a first point having a first tangent and a second point having a second tangent that is perpendicular to the first tangent.

13. The device of claim 3, wherein the at least one movable element comprise an optically transparent material.

14. The device of claim 13, where the device further comprises at least one fixed element comprising an optically transparent material.

15. The device of claim 14, wherein the at least one fixed element is distal to the tubular body and oriented parallel to a longitudinal axis of the device.

16. The device of claim 15, wherein the handle comprises a pivot member and a device-locking mechanism.

17. The device of claim 16, wherein the device-locking mechanism is configured to secure an endoscopic system.

18. The device of claim 3, wherein the at least one movable element comprises a convex outer surface.

19. The device of claim 18, wherein the at least one movable element comprises a concave inner surface.

20. The device of claim 1, further comprising a handle at the proximal end of the tubular body.

21. The device of claim 20, wherein the handle further comprises a pivot member configured to control the configuration of the retractor assembly and a pivot member lock configured to restrict the movement of the pivot member.

22. The device of claim 20, wherein the handle further comprises resistance mechanisms to set the actuation force of the pivot member.

23. The device of claim 20, wherein the handle further comprises a bias member configured to exert a bias force against the pivot member.

24. The device of claim 20, wherein the handle comprises one or more ports.

25. The device of claim 24, wherein at least one port is configured as a flush port.

26. The device of claim 24, wherein at least one port is a visualization port in communication with the at least one lumen configured to hold the endoscopic system.

27. The device of claim 1, wherein the at least one lumen configured to hold the endoscopic system is configured to removably receive the endoscopic system.

* * * * *